(12) United States Patent
Miller

(10) Patent No.: US 9,267,168 B2
(45) Date of Patent: Feb. 23, 2016

(54) METHODS AND COMPOSITIONS FOR ISOLATING TEMPLATE NUCLEIC ACIDS

(71) Applicant: Pacific Biosciences of California, Inc., Menlo Park, CA (US)

(72) Inventor: Erik Miller, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 42 days.

(21) Appl. No.: 13/915,366

(22) Filed: Jun. 11, 2013

(65) Prior Publication Data

US 2013/0330722 A1 Dec. 12, 2013

Related U.S. Application Data

(60) Provisional application No. 61/658,747, filed on Jun. 12, 2012.

(51) Int. Cl.
*C12Q 1/68* (2006.01)
*C12N 15/10* (2006.01)

(52) U.S. Cl.
CPC .......... *C12Q 1/6806* (2013.01); *C12N 15/1003* (2013.01); *C12N 15/1013* (2013.01)

(58) Field of Classification Search
None
See application file for complete search history.

(56) References Cited

U.S. PATENT DOCUMENTS

| | | | |
|---|---|---|---|
| 6,210,891 B1 | 4/2001 | Nyren | |
| 6,833,246 B2 | 12/2004 | Balasubramanian | |
| 6,917,726 B2 | 7/2005 | Levene | |
| 6,936,702 B2 | 8/2005 | Williams | |
| 7,033,764 B2 | 4/2006 | Korlach | |
| 7,041,812 B2 | 5/2006 | Kumar | |
| 7,052,847 B2 | 5/2006 | Korlach | |
| 7,056,676 B2 | 6/2006 | Korlach | |
| 7,170,050 B2 | 1/2007 | Turner | |
| 7,315,019 B2 | 1/2008 | Turner | |
| 7,361,466 B2 | 4/2008 | Korlach | |
| 7,416,844 B2 | 8/2008 | Korlach | |
| 8,003,330 B2 | 8/2011 | Heiner | |
| 8,153,375 B2 | 4/2012 | Travers | |
| 2007/0134128 A1 | 6/2007 | Korlach | |
| 2008/0009007 A1 | 1/2008 | Lyle | |
| 2009/0280538 A1 | 11/2009 | Patel | |
| 2009/0298075 A1 | 12/2009 | Travers | |
| 2010/0081128 A1* | 4/2010 | Drmanac et al. | 435/6 |
| 2011/0183320 A1 | 7/2011 | Flusberg | |
| 2011/0281768 A1 | 11/2011 | Travers | |
| 2012/0071359 A1 | 3/2012 | Sun | |
| 2012/0196279 A1 | 8/2012 | Underwood | |
| 2012/0263783 A1* | 10/2012 | Messmer | 424/450 |
| 2012/0322666 A1 | 12/2012 | Pham | |
| 2012/0322692 A1 | 12/2012 | Pham | |

FOREIGN PATENT DOCUMENTS

WO  WO 2012/065043   5/2012

OTHER PUBLICATIONS

Blackwell, et al., Science, vol. 250, p. 1149-1151, Nov. 23, 1990.
Kadonaga, et al., PNAS, vol. 83, p. 5889-5893, 1986.
Ren, et al., Science, vol. 290, p. 2306-2309, 2000.
Leblanc et al., Biochemistry, vol. 37, No. 17, p. 6015-6022, 1998.
Weber, M., et al., Nat. Genet. vol. 37, No. 853, 2005.

* cited by examiner

*Primary Examiner* — Stephanie K Mummert
*Assistant Examiner* — Aaron Priest
(74) *Attorney, Agent, or Firm* — Morgan, Lewis & Bockius LLP

(57) ABSTRACT

The present invention is directed to methods and compositions for isolating template nucleic acids containing target sequences of interest, wherein those isolated template nucleic acids can be further assessed for information related to sequence and nucleic acid modifications.

13 Claims, 5 Drawing Sheets

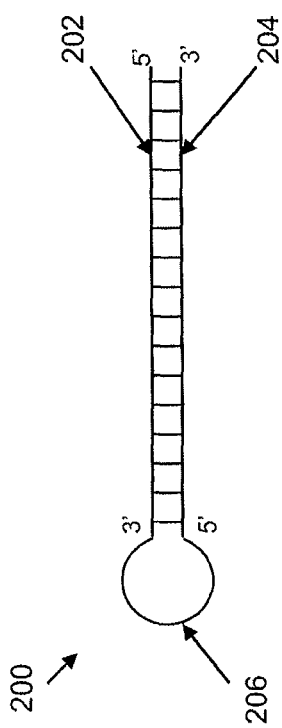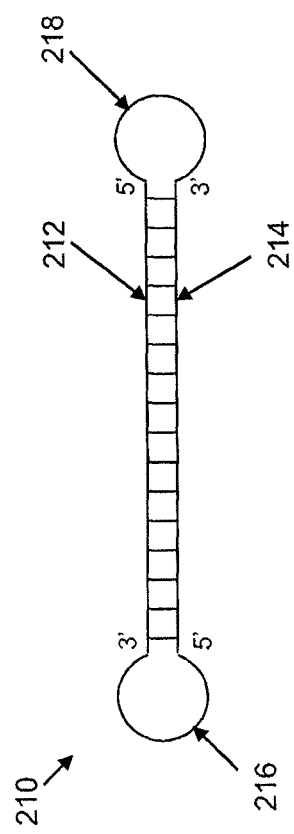

METHODS AND COMPOSITIONS FOR ISOLATING TEMPLATE NUCLEIC ACIDS

STATEMENT REGARDING FEDERALLY SPONSORED RESEARCH

Not applicable.

BACKGROUND OF THE INVENTION

The ability to understand the genetic code has yielded advances in countless areas. From the ability to diagnose disease to the ability to identify evolutionary connections and/or diversity, to the ability to manipulate the genetic framework in the development of new materials and compositions, this understanding has opened doors to advances that have benefited and will continue to benefit biomedical research.

Integral to these advances have been developments in technology directed to the reading and/or characterization of the genetic code. For example, development of nucleic acid sequencing technologies has allowed for the base by base identification of the nucleic acid sequences that make up the genetic code to the point that entire human genomes have been elucidated. Other advances include rapid array based technologies that allow reasonably facile identification of genetic patterns from patients or other biological samples.

One area of development in the analysis of the genetic code is the ability to assess the variety of modifications that can occur in nucleic acids. Such modifications include chemical modifications, variations in nucleic acid conformation or composition, interactions of an agent with a nucleic acid (e.g., bound to the nucleic acid), and other perturbations associated with the nucleic acid.

One challenge in assessing modifications of nucleic acids, particularly genomic DNA, is that many technologies rely on amplified samples for assessment of nucleic acids. However, many nucleic acid modifications (including, for example, methylation) are not retained through the amplification process. The inability to retain these modifications in amplified samples can further contribute to the difficulty of identifying the portions of a nucleic acid sample that contain modifications and separating those nucleic acids from those that do not contain such modifications.

BRIEF SUMMARY OF THE INVENTION

Accordingly, the present invention is generally directed to methods and compositions for isolating template nucleic acids that contain target sequences. These target sequences will in some embodiments comprise nucleic acids modifications.

In one aspect, the present invention provides a method for isolating template nucleic acids containing one or more target sequences where the method includes the steps of: (a) providing a population of circular template nucleic acids, wherein a plurality of the population of circular template nucleic acids comprises the one or more target sequences; (b) amplifying the population of template nucleic acids with a strand displacing polymerase to produce amplified template nucleic acids comprising the circular template nucleic acids and linear nascent strands comprising at least one copy of a sequence complementary to the one or more target sequences; (c) applying one or more affinity handles to the amplified template nucleic acids, wherein the one or more affinity handles associate with the at least one complement of the one or more target sequences; (d) separating amplified template nucleic acids associated with the affinity handles from amplified template nucleic acids not associated with the affinity handles; thereby isolating the template nucleic acids containing one or more target sequences.

In a further embodiment and in accordance with the above, the population of circular template nucleic acids comprises genomic DNA.

In a still further embodiment and in accordance with any of the above, the circular template nucleic acids comprise a single-stranded portion and a double-stranded portion.

In a yet further embodiment and in accordance with any of the above, the circular template nucleic acids are single stranded or double stranded.

In a further embodiment and in accordance with any of the above, the template nucleic acids comprise: (a) a first strand segment, (b) a second strand segment substantially complementary to the first strand segment; (c) a first linking oligonucleotide segment joining the 3' end of the first strand segment to the 5' end of the second strand segment; (d) a second linking oligonucleotide segment joining the 5' end of the first strand segment to the 3' end of the second strand segment.

In a further embodiment and in accordance with any of the above, the affinity handles include an oligonucleotide or a protein capable of binding to a nucleic acid. In an exemplary embodiment, the oligonucleotide comprises deoxynucleotide bases, ribonucleotide bases, or a combination of both deoxynucleotide and ribonucleotide bases. In further exemplary embodiments, the oligonucleotide includes modified nucleotide bases.

In a further embodiment and in accordance with any of the above, the affinity handle includes an oligonucleotide that further comprises a moiety that is a member selected from: biotin, a magnetic bead, a second oligonucleotide, an organic molecule, a polypeptide, a nucleic acid binding dye, a particle, an antibody.

In a further embodiment and in accordance with any of the above, the amplified template nucleic acids produced in accordance with the invention comprise a circular template nucleic acid and a linear amplification product.

In a further embodiment and in accordance with any of the above, methods of the invention further include a step of treating the isolated amplified template nucleic acids such that the circular template nucleic acids are separated from the linear amplification products. In exemplary embodiments, this treating step can include heating the isolated amplified template nucleic acids to separate the circular template nucleic acids from the linear amplification products or applying an exonuclease such that the linear amplification products are digested, leaving only the circular template nucleic acids.

In a further embodiment and in accordance with any of the above, the affinity handles associate with the target sequences by hybridizing or binding to least a portion of the complement of the target sequences.

In a further embodiment and in accordance with any of the above, the amplifying step of methods of the invention are allowed to proceed for a sufficient amount of time such that the linear nascent strand comprises multiple copies of the sequences complementary to the one or more target sequences.

In a further aspect and in accordance with any of the above, the present invention provides a method for identifying modifications in a sample of genomic DNA, where the method includes the steps of: (a) providing circular template nucleic acids from the sample of genomic DNA; (b) isolating circular template nucleic acids comprising one or more target sequences; (c) identifying one or more primary modifications in the isolated template nucleic acids.

In a further embodiment and in accordance with any of the above, the template nucleic acids include a single-stranded portion and a double-stranded portion. In a yet further embodiment, the double-stranded portion is a result of complementarity between two separate portions of the template nucleic acids.

In a further embodiment and in accordance with any of the above, the isolating step includes (i) amplifying the template nucleic acids; (ii) applying one or more affinity handles to the template nucleic acids, where the one or more affinity handles associate with one or more target sequences; (iii) separating template nucleic acids associated with the affinity handles from template nucleic acids not associated with the affinity handles; thereby isolating the template nucleic acids containing one or more target sequences In a further embodiment and in accordance with any of the above, the modifications detected in accordance with the invention include a member selected from: methylated base, a hydroxymethylated base, HOMedU, β-D-glucosyl-HOMedU, cytosine-5-methylenesulfonate, a pseudouridine base, an 7,8-dihydro-8-oxoguanine base, a 2'-O-methyl derivative base, a nick, an apurinic site, an apyrimidic site, a pyrimidine dimer, a cis-platen crosslinking, oxidation damage, hydrolysis damage, a bulky base adduct, a thymine dimer, a photochemistry reaction product, an interstrand crosslinking product, a mismatched base, a secondary structure, and a bound agent.

In a further embodiment and in accordance with any of the above, the identifying step includes: (i) introducing a further modification into the template nucleic acids to produce modified template nucleic acids; (ii) providing an enzyme capable of processing the modified template nucleic acids; (iii) contacting the modified template nucleic acids with the enzyme; (iv) monitoring processing of the modified template nucleic acids by the enzyme; and (v) detecting a change in the processing, where the change is indicative of the further modification, thereby identifying the one or more primary modifications.

In a further aspect and in accordance with any of the above, the present invention provides a method for isolating genomic DNA associated with genes actively expressed in a sample. Such a method includes the steps of: (a) providing mRNA and genomic DNA from the sample; (b) producing template nucleic acids from the genomic DNA; (c) amplifying the template nucleic acids to produce amplified template nucleic acids; (d) hybridizing the amplified template nucleic acids to the mRNA to produce hybridized constructs; (e) separating the hybridized constructs from mRNA and amplified template nucleic acids that are not part of hybridized constructs; thereby isolating genomic DNA associated with genes actively expressed in a sample.

BRIEF DESCRIPTION OF THE DRAWINGS

FIG. 2A-B are schematic illustrations of template nucleic acids of the invention.

DETAILED DESCRIPTION OF THE INVENTION

Figure 1:
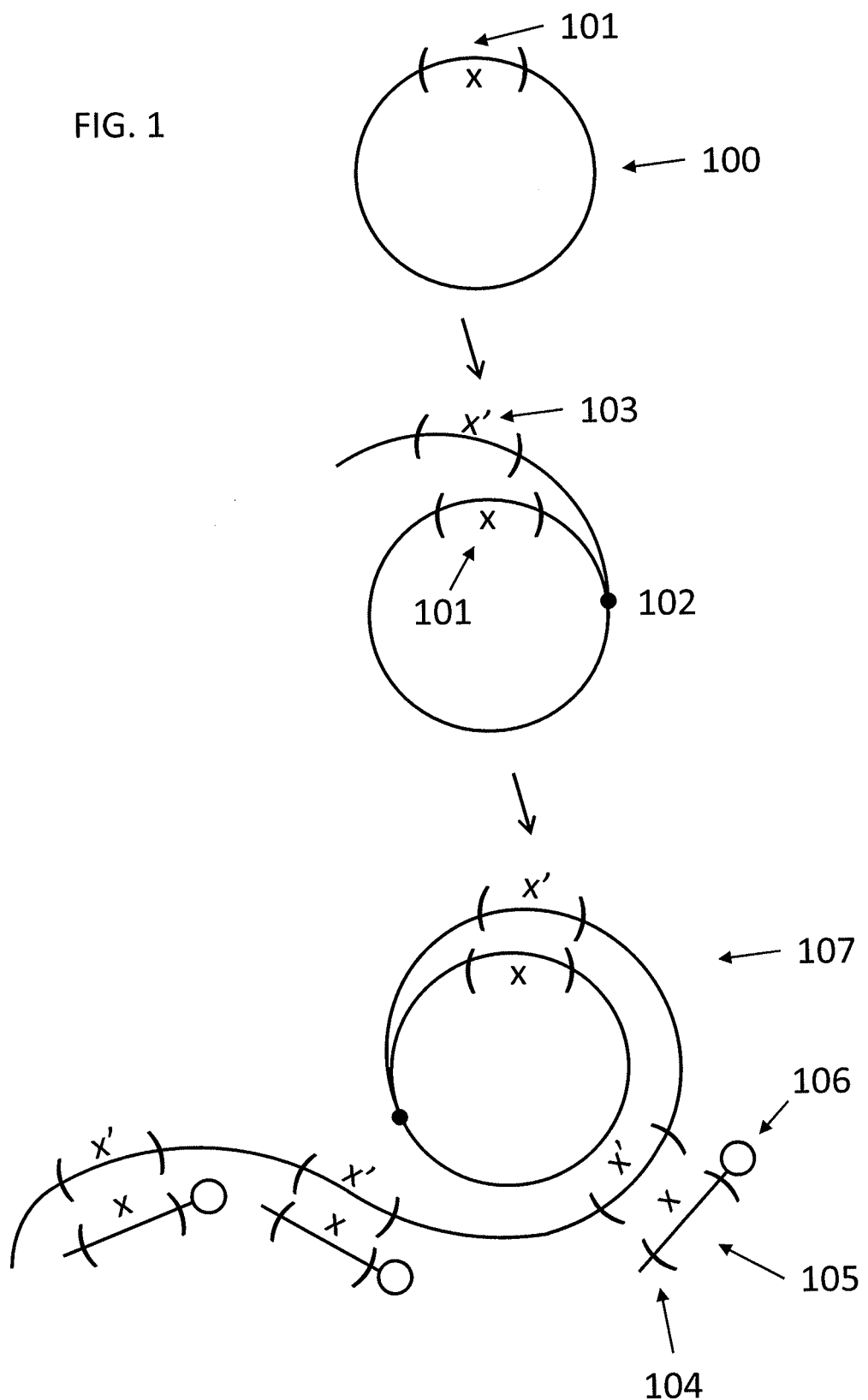
FIG. 1 is a schematic illustration of an embodiment of the invention.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry,* $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

I. Overview

The present invention provides compositions and methods for isolating template nucleic acids containing one or more target sequences. These target sequences will in some exemplary embodiments contain nucleic acid modifications that can be detected and assessed using methods known in the art and described herein.

In specific aspects, the present invention allows sequence-specific purification of genomic DNA. In further aspects, the genomic DNA is in the form of template nucleic acids, including circular nucleic acids or SMRTbell™ constructs known in the art and described herein (see e.g., U.S. Patent Application Publication Nos. 20090280538, filed Mar. 27, 2009 and U.S. Pat. No. 8,153,375, all of which are incorporated by reference herein in their entireties for all purposes, and in particular for all teachings related to circular nucleic acid templates). The purified template nucleic acids of the present invention are suitable for single-molecule sequencing or biochemical analysis, including without limitation mass spectrometry analysis of bases in and around a target sequence to analyze the levels and types of modification.

In general, the present invention provides circular template nucleic acids containing one or more target sequences. The circular template nucleic acids are amplified, generally using a strand displacing polymerase, to produce amplified template nucleic acids. In embodiments in which a strand displacing polymerase is used, the nascent strand (also referred to herein as the "growing strand") that is produced is displaced from the template nucleic acid as the polymerase proceeds around the circular template. The displaced growing nascent strand is a single-stranded nucleic acid that contains one or more copies of the complements of the one or more target sequences contained in the template nucleic acids. The longer the polymerase is allowed to produce a complementary strand to the strand of the template nucleic acid it is using as a template for synthesis, the longer the displaced nascent strand will be, and the more copies of the complement to the one or more target sequences the nascent strand will contain. The amplified template nucleic acids will thus include both the original circular template nucleic acid as well as the growing strand of amplified nucleic acid produced by the polymerase, where the growing strand is at least partially displaced from the circular template nucleic acid.

In preferred aspects of the invention, affinity handles are applied to the amplified template nucleic acids. These affinity handles comprise capture regions that are able to associate with the complements of the one or more target sequences that are contained in the nascent strand produced by the polymerase. In exemplary embodiments, the capture regions of affinity handles of the invention comprise nucleic acid sequences that are able to hybridize to at least a portion of the complements of the one or more target sequences that are contained in the nascent strand.

The affinity handles further contain retrieval moieties through which the affinity handles (and template nucleic acids with which they are associated) can be captured on a surface or a substrate. Affinity handles that are associated with an amplified template nucleic acids can thus be used to retrieve those amplified template nucleic acids and immobilize them on a surface or substrate. By immobilizing the amplified template nucleic acids in this way, the amplified template nucleic acids containing the target sequences of interest can be separated from template nucleic acids that do not contain those target sequences.

In further embodiments, after isolating amplified template nucleic acids containing target sequences from those that do not contain those target sequences, the amplified template nucleic acids are then treated to remove the linear amplified strand from the circular template nucleic acids, leaving the original circular template nucleic acids containing the one or more target sequences of interest isolated from the remainder of the original population of template nucleic acids. In certain embodiments, the treatment comprises applying an exonuclease such that the linear part of the amplified template nucleic acid (i.e., the growing strand) is digested, leaving only the original circular template nucleic acid. The template nucleic acids can then be assessed using methods known in the art and discussed herein, including without limitation sequencing methods and methods to detect nucleic acid modifications.

The present invention encompasses one or more components of methods and compositions described in US Publication No. 20110281768, filed on Feb. 1, 2011, International Application No. PCT/US2011/060338, filed Mar. 29, 2012, and International Published Application No. WO 2012/065043, filed on Nov. 11, 2011, each of which is hereby incorporated by reference in its entirety for all purposes and in particular for all teachings related to template nucleic acid constructs, methods of making template nucleic acid constructs, methods of isolating template nucleic acid constructs, and methods of assessing and analyzing nucleic acids.

The following sections provide further detail on the above and additional aspects and embodiments of the present invention.

II. Template Nucleic Acids

The template nucleic acids of the present invention comprise nucleic acids that contain target sequences that are of interest (for example, target sequences that contain a nucleic acid modification). The terms "nucleic acid" or "oligonucleotide" or grammatical equivalents herein mean at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones, non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme.

In specific embodiments, the template nucleic acids of the present invention are circular nucleic acids formed from genomic DNA. In further embodiments, genomic DNA is obtained from a sample and fragmented using methods known in the art (including without limitation mechanical shearing). The DNA fragments are then used as template nucleic acids, or are further processed to produce circular template nucleic acids or other template configurations, such as those described for example in US Patent Publication No. 20110281768 (filed Feb. 1, 2011) and International Patent Application No. PCT/US2012/029830, filed Mar. 20, 2012, each of which is hereby incorporated by reference in its entirety for all purposes and in particular for all teachings related to template nucleic acids and producing template nucleic acid constructs.

In some embodiments, the template nucleic acids are circular. In further embodiments, the circular template nucleic acids are fully single stranded or fully double stranded. In other embodiments, the circular template nucleic acids comprise a single-stranded portion and a double-stranded portion.

In further embodiments, the template nucleic acids of the invention are generally characterized by the presence of a double stranded segment or a pair of sub-segments that are internally complementary, i.e., complementary to each other. In particular contexts, the target sequence that is included within a template nucleic acid (also referred to herein as "template construct") will typically be substantially comprised of a double stranded segment, e.g., greater than 75%, 80%, 85%, 90%, or 95% of the target segment will be double stranded or otherwise internally complementary. For ease of discussion, these double stranded target segments, whether entirely complementary or predominantly complementary, e.g., having overhang regions, or other non-complementary portions such as secondary loop structures or the like, are referred to herein as complementary or substantially complementary. Where complete complementarity between two strands is intended and required from the context or explicitly, the phrase 'completely complementary' or 'entirely complementary' will be used.

In accordance with the above, template nucleic acids of the invention can include a first strand segment, a second strand segment that is substantially complementary to the first strand segment, a first linking oligonucleotide segment joining the 3' end of the first strand segment to the 5' end of the second strand segment, and a second linking oligonucleotide segment joining the 5' end of the first strand segment to the 3' end of the second strand segment. In further embodiments, the first strand segment and the second strand segment comprise complementary strands of a target sequence.

The template nucleic acid may in further embodiments be provided as a circular or functionally circular construct that allows redundant processing of the same nucleic acid sequence. Use of such circular constructs has been described in, e.g., U.S. Pat. No. 7,315,019 and U.S. Patent Publication No. 2009/0029385, filed Jul. 25, 2008, each of which is hereby incorporated by reference in its entirety for all purposes and in particular for all teachings related to nucleic acid constructs. Alternate functional circular constructs are also described in U.S. Patent Publication No. 2009/0280538, filed Mar. 27, 2009, and U.S. Patent Publication No. 2009/0298075, filed Mar. 27, 2009, the full disclosures of each of which are incorporated herein by reference in their entirety for all purposes, and in particular for all teachings related to nucleic acid constructs.

Briefly, such template nucleic acids can comprise a central double stranded portion that is linked at each end by an appropriate linking oligonucleotide, such as a hairpin loop segment. Such structures not only provide the ability to repeatedly replicate a single molecule, but also provide for additional redundancy by replicating both the sense and antisense portions of the double stranded portion. In the context of sequencing applications, such redundant sequencing provides great advantages in terms of sequence accuracy.

The template nucleic acids can comprise a population of nucleic acids having universal sequence regions that are common to all of the nucleic acids in the population and also have specific regions that are different in the different members of the population. The current invention allows for capturing and isolating template nucleic acids using either the universal or the specific regions. For example, the affinity handles of the invention (which are described in further detail herein) can associate with the specific target sequences or to the universal sequences in template nucleic acids of the invention.

In exemplary embodiments of template nucleic acids that contain both single stranded and double stranded portions, the strands that make up the double stranded segment, and/or the internally complementary strands can be, in the context of the invention, at least partially contiguous, and in preferred aspects are completely contiguous. As used herein, two strands are partially contiguous if they are joined at least one end of each strand, and are completely contiguous if they are joined at both ends, resulting in an overall circular strand configuration, where such joining may be direct coupling of the ends of the sense and antisense strands, or through a linking oligonucleotide. As will be appreciated, the term circular, when referring to the strand configuration merely denotes a strand of a nucleic acid that includes no terminal nucleotides, and does not necessarily denote any geometric configuration.

Examples of template nucleic acid configurations of the invention that are partially and completely contiguous are schematically illustrated in FIGS. 2A and 2B, respectively. In particular, as shown in FIG. 2A, a partially contiguous template sequence 200 is shown which includes a double stranded portion, comprised of two complementary segments 202 and 204, which, for example, represent a target sequence or portion thereof. As shown, the 3' end of segment 202 is linked to the 5' end of segment 204 by linking oligonucleotide 206, providing a single stranded portion of the template, and yielding a partially contiguous sequence. By comparison, as shown in FIG. 2B, a completely contiguous template sequence 210 is shown. Sequence 210 includes a double stranded portion again comprised of two complementary segments 212 and 214. As with the partially contiguous sequence of FIG. 2A, the 3' end of segment 212 is joined to the 5' end of segment 214 via oligonucleotide 216 in a first single stranded portion. In addition, the 5' end of segment 212 is joined to the 3' end of segment 214 via linking oligonucleotide 218, providing a second single stranded portion, and yielding a completely contiguous or circular template nucleic acid.

Further embodiments of components of template nucleic acids of the invention, including methods of making such template nucleic acids, are described for example in US Patent Publication No. 20110281768 (filed Feb. 1, 2011), International Publication No. WO 2012/065403, filed Nov. 11, 2011, and International Patent Application No. PCT/US2012/029830, filed Mar. 20, 2012, each of which is hereby incorporated by reference in its entirety for all purposes and in particular for all teachings related to template nucleic acids and producing template nucleic acid constructs.

In general, the overall size of the template nucleic acid will be dictated by the application in which the template will be used. By way of example, where a given template is being subjected to a polymerase mediated sequencing process, limitations on the readlength for the particular system may be factored into the selection of the overall template size, e.g., to ensure complete, and preferably redundant sequencing of the entire template. For example, where a given polymerase mediated sequencing process has readlength of 1000 bases, a requirement for at least 2× redundant sequencing would dictate a template nucleic acid of 500 bases, including both the linking oligonucleotides and the target sequence. Of course, because the sequence of the start/finish linking oligonucleotide may be known and is not relevant to determination of the target sequence, it may not be necessary to obtain 2× redundancy of that segment, and thus a consequent increase in template size could be tolerated. For purposes of certain redundant sequencing applications, a template nucleic acid that is between about 50 and about 500 bases may be desired. In further embodiments, template nucleic acids of about 10-1000, 15-950, 20-900, 25-850, 30-800, 35-750, 40-700, 45-650, 50-600, 55-550, 60-500, 65-450, 70-400, 75-350, 80-300, 85-250, 90-200, 95-150, and 90-100 bases is used. In other applications, where longer readlengths are obtained, or in non-redundant applications, template nucleic acids that are from about 200 to about 50,000 bases in length may be used. In further embodiments, template nucleic acids of about 100-100,000; 150-90,000; 200-85,000; 250-80,000; 300-75,000; 350-70,000; 400-65,000; 450-60,000; 500-55,000; 550-50,000; 600-45,000; 650-40,000; 700-35,000; 750-30,000; 800-25,000; 850-20,000; 900-15,000; 950-10,000; and 1,000-5,000 bases are used. Although described in terms of specific lengths, it will be appreciated that a variety of different template sizes may be employed for a variety of different specific applications.

In addition to readlength considerations, an overall template may be subject to application-specific structural requirements. For example, where a sequencing process employs nanostructured reaction regions, it may be desirable to provide smaller template molecules to ensure rapid diffusion into and out of the reaction region. For circular templates of the invention, including templates in the SMRTbell™ format discussed herein, any size template would have accessible ends for nanostructured reaction regions. In further embodiments, template molecules of about 100 to about 2000 base pairs are used in accordance with the present invention when utilizing reaction regions on the nanometer or micrometer scale. In still further embodiments, template molecules of about 150-1900, 200-1800, 250-1700, 300-1600, 350-1500, 400-1400, 450-1300, 500-1200, 550-1100, 600-1000, 650-900, and 700-800 base pairs are used.

The size of the target sequence (also referred to herein as "target segment") may also be varied depending upon the application in which the template nucleic acids is being used. For example, in genomic sequencing applications, e.g., de novo or resequencing processes, longer target segments may be desired in order to reduce the level of duplicate coverage that is required among different fragments. In particular, the ability to sequence template fragments that are in excess of 100, preferably in excess of 200, still more preferably, in excess of 500, in excess of 1000, and even in excess of 10,000 nucleotides in length, provides substantial benefits in genomic assembly from overlapping fragments. In particular, the level of required duplicate coverage for identical sequence portions is substantially reduced by increases in the size of any individual sequence read.

In addition to advantages for long read length sequencing applications, larger target segments also provide advantages in the ability to provide paired end sequence data using single molecule sequencing processes. Briefly, in many sequencing processes, one can obtain sequence context of relatively short sequence reads, by reading the sequence that is disposed at opposing ends of a large target fragment. Typically, this involves the sequencing of a relatively short stretch of bases at either end of a double stranded target segment. From the knowledge that these two sequences are derived from the same template nucleic acid, and optionally, from a general understanding of the size of the fragment, one obtains contextual data for the short sequences. While paired end sequencing has distinct advantages in short readlength sequence processes in providing two pieces of sequence information from a given target, it also is useful in longer read sequence technologies as it provides the ability to obtain contextual "waypoints" for very large nucleic acid sequences, which can be used in aligning sequence data.

In the context of the template nucleic acids of the invention, one can readily obtain sequence data from opposing ends of a single template nucleic acid by first obtaining sequence data from a first end of the target sequence. One may then wait an appropriate amount of time for a given sequencing system, for the process to reach the opposing end of the target, and begin obtaining sequence data again. As a result, one has obtained sequence data from paired ends of the same target. As will be appreciated, the foregoing process has particular use where an overall readlength of a sequencing system is impacted by the data collection process, e.g., through the continuous illumination of the complex (See, e.g., U.S. Patent Application No. 2007-0161017, the full disclosure of which is incorporated herein by reference in its entirety for all purposes and in particular for all teachings related to paired end sequencing). Alternatively, one may employ a reaction stop point within the template sequence, such as a reversibly bound blocking group at one location on the template, e.g., on the single stranded portion that was not used in priming. By way of example, and with reference to FIG. 2B, following initial sequencing from the original priming location, e.g., at single stranded linking oligonucleotide portion 216, through one end of the sense strand 214, the data acquisition may be switched off, allowing the polymerase to proceed around the template, e.g., through sense strand 214, to the other previously single stranded portion, e.g., linking oligonucleotide portion 218. The incorporation of a synthesis blocking group coupled to the linking oligonucleotide will allow control of initiation of the sequencing of the opposing end of the antisense strand, e.g., strand 212. One would thereby obtain paired end sequence data for the overall double stranded segment. A variety of synthesis controlling groups may be employed, including, e.g., large photolabile groups coupled to the nucleobase portion of one or more bases in the single stranded portion, which inhibit polymerase mediated replication, strand binding moieties that prevent processive synthesis, non-native nucleotides included within the primer (as described in greater detail elsewhere herein), and the like.

Alternatively, one may employ primer recognition sites on each of the two linking oligonucleotide sequences employed in a population of like template molecules, e.g., PCR products. By then separately sequencing from each end, one can obtain sequence data from different ends of the same double stranded fragment, and thus obtain the paired end data desired.

In contrast, for diagnostic sequencing applications, it may be necessary only to provide sequence data for a small fragment of DNA, but do so in an extremely accurate sequencing process. For such applications, shorter template nucleic acids and/or target sequences may be employed, thus permitting a higher level of redundancy by sequencing multiple times around a small circular template, where such redundancy provides the desired accuracy. Thus, in some cases, the double stranded target sequence may be much shorter, e.g., from 10 to 200, from 20 to 100 or from 20 to 50 or from 20 to 75 bases in length. In further embodiments, the target sequence is from 5-50, 10-55, 15-50, 20-45, 25-40, 30-35 bases in length. For purposes of the foregoing, the length of the target sequences in terms of bases denotes the length of one strand of the double stranded segment of the template nucleic acid.

While different applications will have different impacts on the length of the target sequence portion that is included in the template molecule, the length and structure of the linking oligonucleotide or single stranded portions of the template may be dictated, at least in part, by structural considerations in addition to application specific criteria. In particular, at a minimum, the linking oligonucleotides are required to be able to form a connecting loop between the 3' end of one strand of a double stranded nucleic acid segment and the 5' end of the other strand. As such, where employed primarily as a linking oligonucleotides, e.g., without accommodating larger functional elements, the linking oligonucleotide typically will be from about 4 nucleotides to about 100 nucleotides or more, while linking oligonucleotides of from 4 nucleotides to about 20 nucleotides will be generally preferred. For example, where short linkages are desired, linking oligonucleotides may be from 4 to about 8 nucleotides in length. In further embodiments, linking oligonucleotides are about 4-250, 5-225, 10-220, 15-215, 20-210, 25-200, 30-195, 35-190, 40-185, 45-180, 50-175, 55-170, 60-165, 65-160, 70-155, 75-150, 80-145, 85-140, 90-135, 95-130, 100-125, 105-120 nucleotides in length. In still further embodiments, linking oligonucleotides are about 3-20, 4-19, 5-18, 6-17, 7-16, 8-15, 9-14, 10-13, 11-12 nucleotides in length.

In addition to the foregoing structural requirements, where a given linking oligonucleotide portion provides a primer and/or polymerase binding site, that segment must be of sufficient length to accommodate the desired primer length, as well as a complexed polymerase. Accordingly, linking oligonucleotides that include primer recognition sites will typically be greater than about 20 bases in length, and preferably at least about 36 bases in length. In some cases, it may be desirable to provide sufficient space on one or both sides of the primer within the single stranded portion, e.g., to accommodate polymerase binding, etc. As such, in some cases, the single stranded portion will be substantially greater than as set forth above, e.g., 50 bases, 80 bases, 100 bases or larger.

Notwithstanding the foregoing, in some cases, shorter linking oligonucleotides may be desirable, as templates with smaller hairpin loops show increased efficiency as templates in that less of the overall template construct, and thus, less of the sequencing capability of the system, is taken by the "overhead" of the linking oligonucleotides. Accordingly, linking oligonucleotides in some cases will be smaller than 20 bases in length, preferably smaller than 12 bases in length. As will be appreciated, where one desires to provide optimal primer binding, but enhanced efficiency, the linking oligonucleotides will generally be in the range of from about 20 to about 100 bases in length, preferably, from about 20 to about 80 bases in length. In addition, asymmetric linking oligonucleotides, e.g., having different numbers of nucleotides joining the sense and antisense strands, may be used within a single template construct. Such constructs could be generated through, e.g., iterative processes of cleavage of a sample segment with a first type of restriction endonuclease, followed by annealing/ligation of a first adapter/linking hairpin sequence that is complementary to the cleavage site/overhang sequence, followed by treatment with a second restriction endonuclease, followed by annealing/ligation with a second differently sized hairpin adapter, complementary to the second cleavage site/overhang.

In addition to advantages of consensus potential within each template nucleic acid, and the other advantages described above, the template nucleic acids of the invention further have a number of different advantages for many or all of the different template dependent sequencing processes associated with the potential for the addition of other sequences into the template molecule.

For example, in some cases, connecting or linking sequences may be selected and/or observed as registration sequences to provide landmarks within the overall template sequence, e.g., to provide alignment of iterative sequence data, to identify the level of coverage in a consensus sequence read, to identify points in a sequencing process where one is progressing into a consensus sequence, e.g., an antisense strand or repeated sequence of the entire template, and the like.

In addition, such sequences may provide control opportunities for the sequencing process using such templates. For example, and preferably in the case of completely contiguous sequences, as discussed previously, one may incorporate primer recognition sequences within the connecting oligonucleotides to initiate polymerization. As noted previously, the flexibility as to the types and configuration of the primer sequences is increased by virtue of immunity from binding to the target portion of the sequence, which in preferred embodiments exists as a double stranded segment.

Additional control sequences may also be provided, e.g., sequences that allow control over the initiation of synthesis, e.g., through a hybridized probe or reversibly modified nucleotide, or the like (See, e.g., U.S. Patent Application No. 2008-0009007, the full disclosure of which is incorporated herein by reference in its entirety for all purposes and in particular for all teachings related to initiation of synthesis.). Other control sequences may include binding sites for transcription factors. For example, repressor binding regions may be provided as control sequences within the linking oligonucleotides, such as the lac repressor recognition sequence, which when bound by the lac repressor protein, has been shown to block replication both in vivo and in vitro. Reinitiation of replication is accomplished through the addition of appropriate initiators, such as isophenylthiogalactoside (IPTG) or allolactose. Other DNA binding protein recognition sites may also be included within the linking oligonucleotide to allow control over the progress of synthesis using the templates of the invention. Other controllable elements may include the use of non-natural bases (also termed $5^{th}$ bases) within the linking region that are not paired with any of the four basic nucleoside polyphosphates in the synthesis reaction. Upon encountering such a base, the polymerase would pause until its own particular complement was added to the reaction mixture. Likewise, an engineered pause point within the linking oligonucleotide region could include a "damaged" base that causes a stop in replication until repair enzymes are added to the mixture. For example within the linking oligonucleotide could be included a base position having a pyrimidine dimer. Such compounds would cause the replication complex to pause. Addition of the photolyase DNA repair enzyme would repair the problem location and allow replication, and sequencing to continue.

Recognition sites for a variety of other oligonucleotide probes are also optionally incorporated into these linking sequences, e.g., hybridization sites for labeled probes, molecular beacons, TaqMan® probes, Invader® probes (Third Wave Technologies, Inc.), or the like, that can be used to provide other indications of the commencement of synthesis. Additionally, non-native bases that interact/complement other non-native bases may be used to provide an initiation point for synthesis and sequencing.

In some cases, it may be desirable to provide endonuclease recognition sites within the linking oligonucleotide, which can allow for a mechanism to release a given template sequence from a synthesis reaction, i.e., by linearizing it, and allowing the polymerase to run off the linear template, and/or to expose the template to exonuclease activity, and thus terminate synthesis through removal of the template. Such sites could additionally be exploited as control sequences by providing specific binding locations for endonucleases engineered to lack cleavage activity, but retain sequence specific binding.

In some cases, nicking sites, e.g., sites recognized by nicking endonucleases, may be included within a portion of the template molecule, and particularly within the double stranded portion of the template, e.g., in the double stranded fragment portion or in the stem portion of an exogenous hairpin structure. Such nicking sites provide a break in one strand of a double stranded sequence, to present a priming location for, e.g., a strand displacing polymerase enzyme. In the context of the templates of the invention, the nicking site may be provided for example, within a hairpin adapter that is annealed and ligated to a double stranded target fragment. Other methods known in the art and described in the art may similarly introduce nicking sites. Alternatively, nicking endonucleases may be applied randomly against the target fragment to initiate priming. A variety of nicking enzymes and their recognition sequences are known in the art, with such enzymes being generally commercially available, e.g., from New England Biolabs. Alternatively, one may employ pre-nicked double stranded segments in the hairpin adapters used in preparing the template construct. Such nicks could include gaps in the double stranded segments of from 0 to 20 nucleotides, depending upon the need of the application.

Methods of making template nucleic acids of the invention, particularly template nucleic acids comprising both single stranded and double stranded portions, are described in US Patent Publication No. 20110281768, filed Feb. 1, 2011 which is hereby incorporated by reference in its entirety for all purposes and in particular for all teachings related to the preparation of template nucleic acids (which are also referred to as "contiguous templates" and "templates" in US Patent Publication No. 20110281768).

III. Affinity Handles

In one aspect, the present invention provides affinity handles for use in methods of isolating template nucleic acids that contain target sequences.

Affinity handles of the invention are constructs that comprise a capture domain (also referred to herein as a "capture region") that can associate with a target sequence. Affinity handles of the invention further include a retrieval moiety that can be used to retrieve the affinity handle (also referred to herein as a "retrieval domain" or a "retrieval portion"). Retrieving the affinity handle can include without limitation immobilizing the affinity handle to a substrate. As will be appreciated, when the affinity handle is associated with a target sequence of a template nucleic acid through the capture domain, retrieving the affinity handle through the retrieval domain will also in turn retrieve the associated template nucleic acid.

The capture domains of affinity handles of the invention can be directly connected to the retrieval region, or the affinity handle can comprise an intermediate region connecting the capture and retrieval portions.

The capture domains of affinity handles of the invention are generally designed to be able to associate with template nucleic acids of the invention or with complements of target sequences produced through, for example, use of a strand displacing polymerase. In preferred embodiments, the capture domains hybridize or bind to at least a portion of target sequences in template nucleic acids of the invention or to the complements of those target sequences produced through amplification of the template nucleic acid. This hybridization or binding can be reversible. The capture region will generally be designed both to have efficient and specific binding, and also such that the binding is reversible, allowing for separation of the affinity handle from the template nucleic acid after isolation. In exemplary embodiments, the capture domains comprise an oligonucleotide or a protein capable of binding to a nucleic acid. In embodiments in which the capture domains comprise an oligonucleotide, that oligonucleotide may comprise deoxynucleotide bases, ribonucleotide bases, or a combination of both deoxynucleotide and ribonucleotide bases. The oligonucleotide may further comprise nucleotide analogs (modified nucleotides) and/or nucleoside polyphosphates comprising three or more phosphate groups.

As discussed herein, the capture and retrieval domains of affinity handles of the invention may comprise nucleotides. The nucleotides used in the invention, whether natural, unnatural, modified or analog, are suitable for hybridization or binding to a target sequence. The term nucleotide may also be used to refer to nucleotides having other than three phosphate groups, for example 4, 5, 6, 7 or more phosphate groups. Such nucleotides have been described, for example in U.S. Pat. Nos. 6,936,702 and 7,041,812, which are each hereby incorporated by reference in their entirety for all purposes and in particular for all teachings related to nucleotides.

The nucleotide compositions may include nucleoside triphosphates, or analogs of such compounds. For example, in some cases, the reaction mixtures will include nucleotide analogs having longer phosphate chains, such as nucleoside tetra, penta-, hexa- or even heptaphosphates. In addition, the nucleotide analogs of the compositions of the invention may additionally include other components, such as detectable labeling groups. Such detectable labeling groups will typically impart an optically or electrochemically detectable property to the nucleotide analogs being incorporated into the synthesis reaction. In particularly preferred aspects, fluorescent labeling groups, i.e., labeling groups that emit light of one wavelength when excited with light of another wavelength, are used as the labeling groups. For purposes of the present disclosure, the foregoing or later discussed nucleotide or nucleotide analog compositions whether labeled or unlabeled, possessing of one or more phosphate groups, typically two or more or three or more phosphate groups, or otherwise modified, are generally referred to herein as nucleotides.

The capture region can also comprise other suitable molecules that specifically bind to a target sequence on the template nucleic acid. For example, the capture region can comprise transcription factors, histones, antibodies, nucleic acid binding proteins, and nucleic acid binding agents, etc., that will bind to a specific sequence. See, e.g. Blackwell et al. Science 23 Nov. 1990:Vol. 250, 1149-1151 and Kadonaga et al. PNAS, 83, 5889-5893, 1986, and Ren et at. Science, 290, 2306-2309, 2000, each of which is specifically incorporated herein by reference for all purposes in its entirety and in particular for all teachings related to capture regions. The capture region can comprise an antibody that is designed to attach to a specific target sequence. For antibodies that recognize specific nucleic acid sequences, see, for example LeBlanc et al., Biochemistry, 1998, 37 (17), pp 6015-6022, which is specifically incorporated herein by reference for all purposes in its entirety and in particular for all teachings related to antibodies that recognize nucleic acid sequences. In some cases, the capture region can comprise agents that will specifically bind regions of the template nucleic acid that have modified or unnatural nucleotides. For example, antibodies against 5-MeC are used to enrich for methylated DNA sequences (See, e.g. M. Weber, et al., Nat. Genet. 2005, 37, 853, incorporated herein by reference in its entirety for all purposes and in particular for all teachings related to methylated DNA sequences). In certain embodiments, the modification is an 8-oxoG lesion and/or the agent is a protein is selected from the group consisting of hOGG1, FPG, yOGG1, AlkA, Nth, Nei, MutY, UDG, SMUG, TDG, or NEIL. In other embodiments, the modification is a methylated base and/or the agent is a protein selected from the group consisting of MECP2, MBD1, MBD2, MBD4, and UHRF1. Specific binding is described also in U.S. Patent Publication No. 20110183320, filed Nov. 12, 2010, which is hereby incorporated by reference in its entirety and in particular for all teachings related to specific binding of agents to methylated bases.

In preferred embodiments, the capture region of an affinity handle of the invention comprises an oligonucleotide with a region that can bind or hybridize to a target sequence contained within a template nucleic acid of the invention or to its complement. Where the capture region comprises an oligonucleotide (also referred to herein as a "capture oligonucleotide"), the length of the capture oligonucleotide can vary depending on the application. It is well known that the strength and selectivity of binding of complementary or partly complementary oligonucleotides can be controlled by controlling the stringency of the medium, including the ionic strength of the solution and the temperature. The capture region will generally be designed both to have efficient and specific binding, and also such that the binding is reversible, allowing for separation of the affinity handle from the amplified template nucleic acid after isolation. In some cases the length of the capture oligonucleotide on the affinity handle is from about 4 to about 100 nucleotides, from about 6 to about 50 nucleotides, or from about 8 to about 25 nucleotides in length. A capture oligonucleotide can comprise natural and/or non-natural nucleotide units, including for example PNA.

The capture region can also comprise other suitable molecules that specifically bind to an exposed sequence on the template nucleic acid. For example, the capture region can comprise transcription factors, histones, antibodies, nucleic acid binding proteins, and nucleic acid binding agents, etc., that will bind to a specific sequence. See, e.g. Blackwell et al. Science 23 Nov. 1990:Vol. 250, 1149-1151 and Kadonaga et al. PNAS, 83, 5889-5893, 1986, and Ren et at. Science, 290, 2306-2309, 2000. The capture region can comprise an antibody that is designed to attach to a specific sequence. For antibodies that recognize specific nucleic acid sequences, see, for example LeBlanc et al., Biochemistry, 1998, 37 (17), pp 6015-6022. In some cases, the capture region can comprise agents that will specifically bind regions of the template nucleic acid that have modified or unnatural nucleotides. For example, antibodies against 5-MeC are used to enrich for methylated DNA sequences (See, e.g. M. Weber, et al., Nat. Genet. 2005, 37, 853, incorporated herein by reference in its entirety for all purposes and in particular for all teachings related to methylated DNA sequences and methods for enriching for them). In certain embodiments, the modification is an 8-oxoG lesion and/or the agent is a protein is selected from the group consisting of hOGG1, FPG, yOGG1, AlkA, Nth, Nei, MutY, UDG, SMUG, TDG, or NEIL. In other embodiments, the modification is a methylated base and/or the agent is a protein selected from the group consisting of MECP2, MBD1, MBD2, MBD4, and UHRF1. Specific binding is described also in U.S. patent application Ser. No. 12/945,767, filed Nov. 12, 2010, which is hereby incorporated by reference in its entirety and in particular for teachings related to specific binding of methylated bases.

As will be appreciated, capture domains used for affinity handles of the present invention may contain any combination of the embodiments described above.

The retrieval region of the affinity handle is provided for removal and isolation of the affinity handle and the template nucleic acid (in preferred embodiments an amplified template nucleic acid) that is associated with the affinity handle. In some embodiments, the retrieval region comprises a bead or other solid surface. In further embodiments, the retrieval region comprises a member of a binding pair which allows for removal of the affinity handle by a bead or surface comprising the other member of the binding pair. The binding pair for retrieval of the affinity handle can bind by hybridization, ionic, H-bonding, Van der Waals or any combination of these forces. In some cases, the retrieval can be done using hybridization, e.g. using specific sequences or by using polynucleotide sequences. For example, one member of the biding pair can comprise either poly(A), poly(dA), poly(C) or poly(dC), and the other binding member can comprise poly(T), poly (dT), poly(G) or poly(dG). The length of the polynucleotide sequence can be chosen to provide the best binding and release properties. The binding and release can be controlled, for example, by controlling the stringency of the solution. Non-natural and modified bases can also be used in order to control the binding and release properties.

Binding members can comprise, e.g., biotin, digoxigenin, inosine, avidin, GST sequences, modified GST sequences, e.g., that are less likely to form dimers, biotin ligase recognition (BiTag) sequences, S tags, SNAP-tags, enterokinase sites, thrombin sites, antibodies or antibody domains, antibody fragments, antigens, receptors, receptor domains, receptor fragments, or combinations thereof.

The retrieval moiety of affinity handles of the invention can in further embodiments be an oligonucleotide sequence, a member of a binding pair, a solid substrate such as a bead, an organic molecule, a polypeptide, a nucleic acid binding dye, a particle, or an antibody. In specific embodiments, the retrieval moiety is biotin.

As discussed above, in some embodiments, the retrieval portion includes a magnetic bead, or comprises a component that is able to bind to a magnetic bead, often through a complementary component on the bead. The template nucleic acid associated with the affinity handle can then be separated from the other components of the mixture by well known methods of magnetic bead purification. As is discussed in further detail herein, isolated template nucleic acid can then be removed from the affinity handle for subsequent use, such as for nucleic acid sequencing. For example, where the affinity handle comprises an oligonucleotide that is hybridized to the complement of the target sequence of a template nucleic acid, the circular template nucleic acid can be released from the nascent strand (and the associated affinity handle) by raising the stringency of the solution, for example by lowering the ionic strength or raising the temperature.

In embodiments that utilize beads as part of the retrieval portion either directly or indirectly, such beads are generally spherical, but can have any other suitable shape, for example fibers, rods, disks, cubes, or other shaped materials can be used. Beads are useful as they can be readily manipulated within a solution. Beads for use in the invention can be functionalized on their outer surfaces for the attachment of affinity handles of the invention. Suitable beads include polymeric beads having functional organic molecules on their surfaces allowing for such attachment. A variety of types of types of beads are known and used and many are commercially available. The beads can be produced in various size ranges from the nanometer to the millimeter size range. In some cases, the beads can be produced to be relatively monodisperse, which can be helpful in obtaining consistent results.

Magnetic beads have been used for purification and separation in chemical and biochemical processes, and functionalized magnetic beads are commercially available. For example, NEB offers a variety of magnetic beads including Amylose Magnetic Beads, Anti-MBP Magnetic Beads, Chitin Magnetic Beads, Goat Anti-Mouse IgG Magnetic Beads, Goat Anti-Rabbit IgG Magnetic Beads, Goat Anti-Rat IgG Magnetic Beads, Hydrophilic Streptavidin Magnetic Beads, Protein A Magnetic Beads, Protein G Magnetic Beads, Streptavidin Magnetic Beads, SNAP-Capture Magnetic Beads, Oligo(dT) Magnetic Beads; Dynal (Life Technologies) offers a variety of functionalized magnetic beads including streptavidin coated beads, beads for binding with His tags, anion exchange, cation exchange, hydrophobic capture, and antibody beads. Micromod offers magnetic beads functionalized with surface functionalities NH2, PEG-NH2 and PEG-COOH for the covalent binding of proteins, antibodies or other molecules. Tubobeads LLC offers beads having streptavidin, sulfonate, carboxylate, or ammonium functionality. Spherotech Inc. offers magnetic beads having a variety of functionalities including carboxyl, amino, antibodies, and proteins. Using functionalized beads and known methods of surface polymer synthesis, beads with a variety of properties can be made, including those having oligonucleotides or peptides having specified sequences.

The beads can comprise polymers including polystyrene/polymethacrylate, dextran, crosslinked dextran, silica-fortified dextran, starch (BNF-starch particles), poly(lactic acid), poly(ethylene imine), or chitosan. The beads can also be made from inorganic material such as carbon, iron oxide, silica, or silicon. The magnetic beads can be useful as long as they are effectively moved by an applied magnetic field. For example, the beads can be ferromagnetic or paramagnetic, or superparamagnetic.

As would be understood in the art, the beads generally do not have a perfectly spherical shape, and are generally not perfectly monodisperse, but will have a distribution of sizes and shapes. In addition, where the outsides surfaces of the particles are composed of polymers that are soluble or partly soluble in the solution, the surfaces are not smooth flat surfaces, but the groups attached to the surface can extend from the bead on polymer chains into the solution. In some cases, spacer or linker molecules are provided on the bead surface between a functional group on the bead and the group that is used to link to the affinity handle. By varying the length of the spacer or linker, one can provide for more or less reach between the surface of the bead and the affinity handle. The spacer or linker can be any suitable molecular structure. It can be made, for example from a polymer such as polypeptide, poly(vinyl alcohol), poly ethylene glycol, or polysaccharide. The linker will generally be made using a polymer that is soluble in the solution that the bead deposition takes place in.

As is discussed above, affinity handles of the invention may contain one or more domains comprising oligonucleotides. The nucleotides or set of nucleotides making up such oligonucleotides are generally naturally occurring nucleotides but can also include modified nucleotides (nucleotide analogs). The term nucleotide may also be used to refer to nucleotides having other than three phosphate groups, for example 4, 5, 6, 7 or more phosphate groups. Such nucleotides have been described, for example in U.S. Pat. Nos. 6,936,702 and 7,041,812, which are hereby incorporated in their entirety for all purposes and in particular for all teachings related to nucleotides.

The nucleotides used to design the affinity handles discussed herein may include nucleoside triphosphates, or analogs of such compounds. For example, in some cases, the reaction mixtures will include nucleotide analogs having longer phosphate chains, such as nucleoside tetra, penta-, hexa- or even heptaphosphates. In addition, the nucleotide analogs of the compositions of the invention may additionally include other components, such as detectable labeling groups. Such detectable labeling groups will typically impart an optically or electrochemically detectable property to the nucleotide analogs being incorporated into the synthesis reaction. In particularly preferred aspects, fluorescent labeling groups, i.e., labeling groups that emit light of one wavelength when excited with light of another wavelength, are used as the labeling groups. For purposes of the present disclosure, the foregoing or later discussed nucleotide or nucleotide analog compositions whether labeled or unlabeled, possessing of one or more phosphate groups, typically two or more or three or more phosphate groups, or otherwise modified, are generally referred to herein as nucleotides. Labels such as fluorescent dye groups may be located in various positions on the nucleotide. In some cases, a fluorescent dye is located on the terminal phosphate of the nucleotide.

IV. Methods of Isolating Template Nucleic Acids Comprising Target Sequences

In one aspect, the present invention provides methods for isolating template nucleic acids containing one or more target sequences. In general, such methods include the steps of (i) providing a population of template nucleic acids; (ii) amplifying the population of template nucleic acids; (iii) applying affinity handles to the amplified template nucleic acids; and (iii) separating the amplified template nucleic acids associated with affinity handles from those that are not associated with an affinity handle.

As used herein, "amplifying" the population of template nucleic acids refers to making multiple copies of those template nucleic acids and/or extending those template nucleic acids or extending the complement of those template nucleic acids, for example through the use of a rolling circle replication/amplification method.

In some embodiments, the population of template nucleic acids comprises circular template nucleic acids. In specific embodiments, the template nucleic acids include one or more target sequences that are of interest for further assessment (such as assessment of nucleic acid modifications), as is discussed in further detail herein. In further embodiments, the template nucleic acids comprise genomic DNA.

In further embodiments, the amplifying step of methods of the invention utilizes a strand displacing polymerase. As is known in the art, the strand displacing polymerase will displace the nascent strand that is complementary to the strand it is using as a template for synthesis. In embodiments utilizing the SMRTbell™ format of template, the first pass of the strand displacing polymerase displaces the complementary fragment of the SMRTbell™ that serves as the second half of the template. At that point, the polymerase enters rolling circle replication and its action of replicating the now circular template will displace the nascent strand (see e.g., U.S. Patent Application Publication Nos. 20090280538, filed Mar. 27, 2009 and U.S. Pat. No. 8,153,375, all of which are incorporated by reference herein in their entireties for all purposes, and in particular for all teachings related to SMRTbell™ and circular nucleic acid templates). In embodiments in which the template nucleic acid is a circular nucleic acid, the strand displacing polymerase can produce multiple copies of the complement of the template nucleic acid strand if allowed to continue to process the template nucleic acid past the point of making a complete circuit around the template. For example, as schematically illustrated in FIG. 1, the template nucleic acid 100 is amplified by stand displacing polymerase 102. The growing nascent strand is at least partially displaced from the strand of template nucleic acid 100 that is being used as a template for synthesis (as will be appreciated, although the template nucleic acid 100 is pictured in FIG. 1 as a single stranded circle, in some embodiments, the template nucleic acid can be double stranded). The template nucleic acid includes a target sequence X (101), and the nascent strand includes the complement of that target sequence X' (103). The longer the polymerase is allowed to proceed around the template nucleic acid, the more copies of the complements of the target sequences will be contained in the nascent strand. The resultant amplified template nucleic acid (107) comprises both the original circular template nucleic acid and the nascent strand generated by the actions of the polymerase.

In still further embodiments and as is also depicted in FIG. 1, affinity handles (104) are applied to the amplified template nucleic acids and associate with the complements of the target sequences (X') contained in the nascent strand. In specific embodiments, the affinity handles contain a capture region (105) that comprises an oligonucleotide sequence that is able to hybridize to at least a portion of the complements of the target sequences X' contained in the nascent strand.

The affinity handles associated with the complements of the target sequences will in further embodiments comprise a retrieval moiety (106) that can be used to separate the affinity handles and their associated amplified template nucleic acids from the remainder of the population of template nucleic acids. In exemplary embodiments, the retrieval moiety can be used to immobilize the complex to a substrate, and the remainder of template nucleic acids that are not associated with an affinity handle can then be removed. Thus, the template nucleic acids containing the one or more target sequences of interest are isolated from the remainder of the population of template nucleic acids. As will be appreciated, the affinity handles may also associate with complements of sequences other than sequences that are of interest for further analysis. In other words, the sequences whose complement the affinity handles associate with may in some embodiments be different sequences from the target sequences that are of interest for further study.

By "substrate" or "solid support" or other grammatical equivalents herein is meant any material that can be modified to contain discrete individual sites appropriate for the attachment or association of nucleic acids. The substrate can comprise a wide variety of materials, as will be appreciated by those skilled in the art, including, but not limited to glass, plastics, polymers, metals, metalloids, ceramics, and organics. When the solid support is a bead, a wide variety of substrates are possible, including but not limited to magnetic materials, glass, silicon, dextrans, and plastics.

In further embodiments, the substrate comprises an array of zero mode waveguides in the form of nanoscale wells in which the nanoscale wells have coupling groups such as biotin on the bases of the wells, resulting in the deposition of isolated template nucleic acids in the zero mode waveguides.

In further embodiments, substrates of use in the invention comprise beads or planar surfaces comprise agents or moieties capable of associating with the retrieval portion of the affinity handles. In exemplary embodiments, the beads or planar surfaces comprise agents or moieties that can hybridize or bind to the retrieval portion of affinity handles of the invention. In further embodiments, such hybridization or binding is reversible.

In some embodiments, the substrates can comprise beads, including magnetic beads. In some cases, beads having poly (T) sequences are used to hybridize to poly(A) regions on the retrieval portions of the affinity handle. The use of magnetic beads for separation of biomolecules is well developed. Once the affinity handles (and their associated amplified template nucleic acids) are attached to the substrates, other components of the reaction mixture (including unbound affinity handles and template nucleic acids that are not associated with affinity handles) can be washed away providing isolation of the template nucleic acids comprising the target sequences of interest. In addition to washing away unbound affinity handles and template nucleic acids, the process can remove other components from the reaction.

In further embodiments, after isolating the amplified template nucleic acids, the amplified strand can be separated from the circular template nucleic acid using methods known in the art and described in further detail herein, including heating in the presence of formamide and then treating with exonucleases. In further embodiments, organic solvents such as formamide, dimethylformamide, dimethyl sulfoxide and denaturing chemicals such as urea or guanidinium chloride are used in methods of separating the circular template nucleic acid from the amplified strand in order to retrieve the target sequences after capture.

Further aspects of methods of isolating template nucleic acids that are known in the art can also be applied to template nucleic acids of the present invention, including methods and compositions discussed in International Patent Application No. PCT/US2012/029830, filed Mar. 20, 2012, which is hereby incorporated by reference in its entirety for all purposes and in particular for all teachings related to template nucleic acids and isolating template nucleic acid constructs.

The following discussion provides further details on methods of the invention. Although the different steps of the method are discussed separately, the present invention encompasses any combination of any of the embodiments discussed herein.

Amplification Steps

In accordance with any of the above, one step of the process for isolating template nucleic acids includes amplification of the template nucleic acid. This amplification can be accomplished using any methods known in the art including without limitation polymerase chain reaction (PCR), strand displacement amplification (SDA), multiple displacement amplification (MDA), rolling circle amplification (RCA), rolling circle replication (RCR) and other amplification (including whole genome amplification) methodologies.

In a preferred embodiment, amplification of the template nucleic acids is accomplished using a strand displacing polymerase. In further embodiments, this amplification can be accomplished using natural and/or non-natural nucleotides. As used in the art, the term nucleotide refers both to the nucleoside triphosphates that are added to a growing nucleic acid chain in the polymerase reaction, and also to refer to the individual units of a nucleic acid molecule, for example the units of DNA and RNA. Herein, the term nucleotide is used consistently with its use in the art. Whether the term nucleotide refers to the substrate molecule to be added to the growing nucleic acid or to the units in the nucleic acid chain can be derived from the context in which the term is used.

The nucleotides or set of nucleotides used during nucleic acid synthesis or amplification in accordance with present invention are generally naturally occurring nucleotides but can also include modified nucleotides (nucleotide analogs). The nucleotides used in the invention, whether natural, unnatural, modified or analog, are suitable for participation in a polymerase reaction. The term nucleotide may also be used to refer to nucleotides having other than three phosphate groups, for example 4, 5, 6, 7 or more phosphate groups. Such nucleotides have been described, for example in U.S. Pat. Nos. 6,936,702 and 7,041,812, which are hereby incorporated in their entirety for all purposes and in particular for all teachings related to nucleotides. Labels such as fluorescent dye groups may also be located in various positions on the nucleotide. In some cases, a fluorescent dye is located on the terminal phosphate of the nucleotide.

As discussed above in the section on affinity handles, nucleotides used in the amplification/synthesis reactions of the present invention may include nucleoside triphosphates, or analogs of such compounds. For example, in some cases, the reaction mixtures will include nucleotide analogs having longer phosphate chains, such as nucleoside tetra, penta-, hexa- or even heptaphosphates. In addition, the nucleotide analogs of the compositions of the invention may additionally include other components, such as detectable labeling groups. Such detectable labeling groups will typically impart an optically or electrochemically detectable property to the nucleotide analogs being incorporated into the synthesis reaction. In some aspects, fluorescent labeling groups, i.e., labeling groups that emit light of one wavelength when excited with light of another wavelength, are used as the labeling groups. For purposes of the present disclosure, the foregoing or later discussed nucleotide or nucleotide analog compositions whether labeled or unlabeled, possessing of one or more phosphate groups, typically two or more or three or more phosphate groups, or otherwise modified, are generally referred to herein as nucleotides.

As will be appreciated, in embodiments in which the template nucleic acids are circular nucleic acids and amplification is accomplished using a strand displacing polymerase, the longer the polymerase is allowed to process the template nucleic acid, the longer the nascent strand will be, and thus the greater the number of copies of the complements of the template nucleic acid, including the complements of the one or more target sequences of interest contained in the template nucleic acid. In certain embodiments, the polymerase is allowed to process the template nucleic acid such that at least a portion of the template nucleic acid is replicated. In further embodiments, the polymerase is allowed to process the template nucleic acid such that at least one copy of the complement of the target sequence(s) is contained in the nascent strand. In still further embodiments, the polymerase is allowed to process long enough such that the nascent strand comprises at least 2-10 copies of the complement to the target sequence(s). In yet further embodiments, the polymerase is allowed to process long enough to allow the nascent strand to contain about 1-100, 2-90, 3-80, 4-70, 5-60, 6-50, 7-40, 8-30, 9-20, 10-15 copies of the complement to the target sequence (s). In other words, the polymerase reaction is controlled to allow the polymerase to process the full template nucleic acid a desired number of times.

Methods for controlling the length of time that a polymerase reaction is allowed to proceed are known in the art, and generally involve controlling the initiation and the halting of the polymerase reaction. For example, it is known that the polymerase can be inactivated fully or partially by including Sr and or Ca in the reaction medium. The level of catalytic metals such as Mg and Mn can also be kept relatively low to minimize the amount of nucleic acid synthesis. Other conditions such as the temperature and the pH can be used to minimize or halt polymerization.

The conditions required for nucleic acid synthesis and amplification are well known in the art. The polymerase reaction conditions include the type and concentration of buffer, the pH of the reaction, the temperature, the type and concentration of salts, the presence of particular additives that influence the kinetics of the enzyme, and the type, concentration, and relative amounts of various cofactors, including metal cofactors.

Methods of initiating or speeding synthesis include simply adding the appropriate reagents for nucleic acid synthesis at the appropriate temperature and pH. Other suitable methods, such as raising the temperature, for example, to initiate synthesis by a hot-start enzyme can also be used. The pH of the reaction can also influence the rate of the polymerase reaction. The temperature of the reaction can be adjusted to enhance the performance of the system. The reaction temperature may depend upon the type of polymerase which is employed.

Enzymatic reactions are often run in the presence of a buffer, which is used, in part, to control the pH of the reaction mixture. Buffers suitable for the invention include, for example, BIS-TRIS propane (BTS), TAPS (3-{[tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl] amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

One method of controlling the length of time that a template nucleic acid is amplified in a controllable fashion is to carry out polymerization for a specific period of time under controlled conditions, at which point the enzyme synthesis activity is halted. The controlled conditions will usually involve controlling reaction conditions such that the polymerase performs synthesis more slowly than it is capable of. Slowing and controlling the enzyme can be done, for example, by adding a non-catalytic metal such as Ca. In some cases, only Ca is added as a divalent metal. In some cases, an appropriate ratio of catalytic to non-catalytic metal divalent cation will be provided to obtain the desired rate. The ratio of Ca to Mg or Mn can be from about 10 to about 200, from about 3 to about 1000, or from about 1 to about 10000.

One method of halting the reaction is to add a reagent that causes the enzyme to stop polymerizing, but keeps the enzyme intact for further polymerization. A preferred reagent for halting the polymerase is Sr. Adding Sr at the appropriate concentration, the polymerase reaction can be reversibly halted. The concentration of Sr to halt the polymerase can be, for example, from about 0.2 mM to about 20 mM, from about 0.01 mM to about 100 mM, or from about 1 nM to about 0.5 M.

The time between initiation and halting can be from on the order of seconds to on the order of days. Where the reaction time is fast, on the order of seconds, it can be more difficult to control the initiation and termination throughout the volume of the reaction. Where the reaction time is multiple hours, there is the disadvantage of having to wait a long time. Therefore, reaction times from about 10 seconds to about 4 hours, about 30 seconds to about 2 hours, or about 1 minute to about 30 minutes are desirable.

Another method of halting the polymerase reaction is to add reagents which bind the catalytic metal. It is known, for example, that a chelating agent such as EDTA can complex with the catalytic divalent cations to halt the reaction. Chelating agents must be used with care, as if the divalent cations are complexed too effectively, it can result in a destabilization of the polymerase-nucleic acid complex. The reaction can also be halted by changing the conditions, such as the temperature and the pH in a manner that halts enzyme polymerization. As with chelating agents these halting methods must be carried out with care so as not to damage the polymerase-nucleic acid complex, e.g. by denaturing the enzyme. For example, lowering of the temperature can be used to halt the reaction reversibly either alone or in combination with other methods.

In some cases, halting can be accomplished by providing only a limiting amount of reagents for the synthesis reaction. For example, the nucleotide or nucleotide analog can be provided at an amount such that the reaction runs out or slows down significantly as the desired amount of walk-in is reached.

Further methods for amplifying template nucleic acids are known in the art and described for example in US Publication No. 20110281768, filed on Feb. 1, 2011, International Application No. PCT/US2011/060338, and International Published Application No. WO 2012/065043, filed on Nov. 11, 2011, each of which is hereby incorporated by reference in its entirety for all purposes and in particular for all teachings related to amplifying, synthesizing, and or making template nucleic acid constructs, which as will be appreciated, may be referred to using grammatical equivalents to the term "template nucleic acids" as used herein.

While in many cases nucleic acid synthesis and amplification is describe herein as extending from a primer, it is to be understood that some polymerases do not require an added external primer, and can be initiated using terminal protein. Polymerases that can be initiated using terminal protein include phi-29 polymerase.

The polymerase enzymes used in the invention will generally have strand-displacement activity. Many polymerases have this capability, and it is useful in the context of the current invention for opening up and exposing the regions of a nucleic acid sample for capture by an affinity handle. In some cases, strand displacement is part of the polymerase enzyme itself In other cases, other cofactors or co-enzymes can be added to provide the strand displacement capability.

DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol. Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies;

PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. No. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SFS, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. patent application Ser. Nos. 12/924,701, filed Sep. 30, 2010; and 12/384,112, filed Mar. 30, 2009.

In further embodiments, the polymerase enzyme used in the methods of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Figure 4:
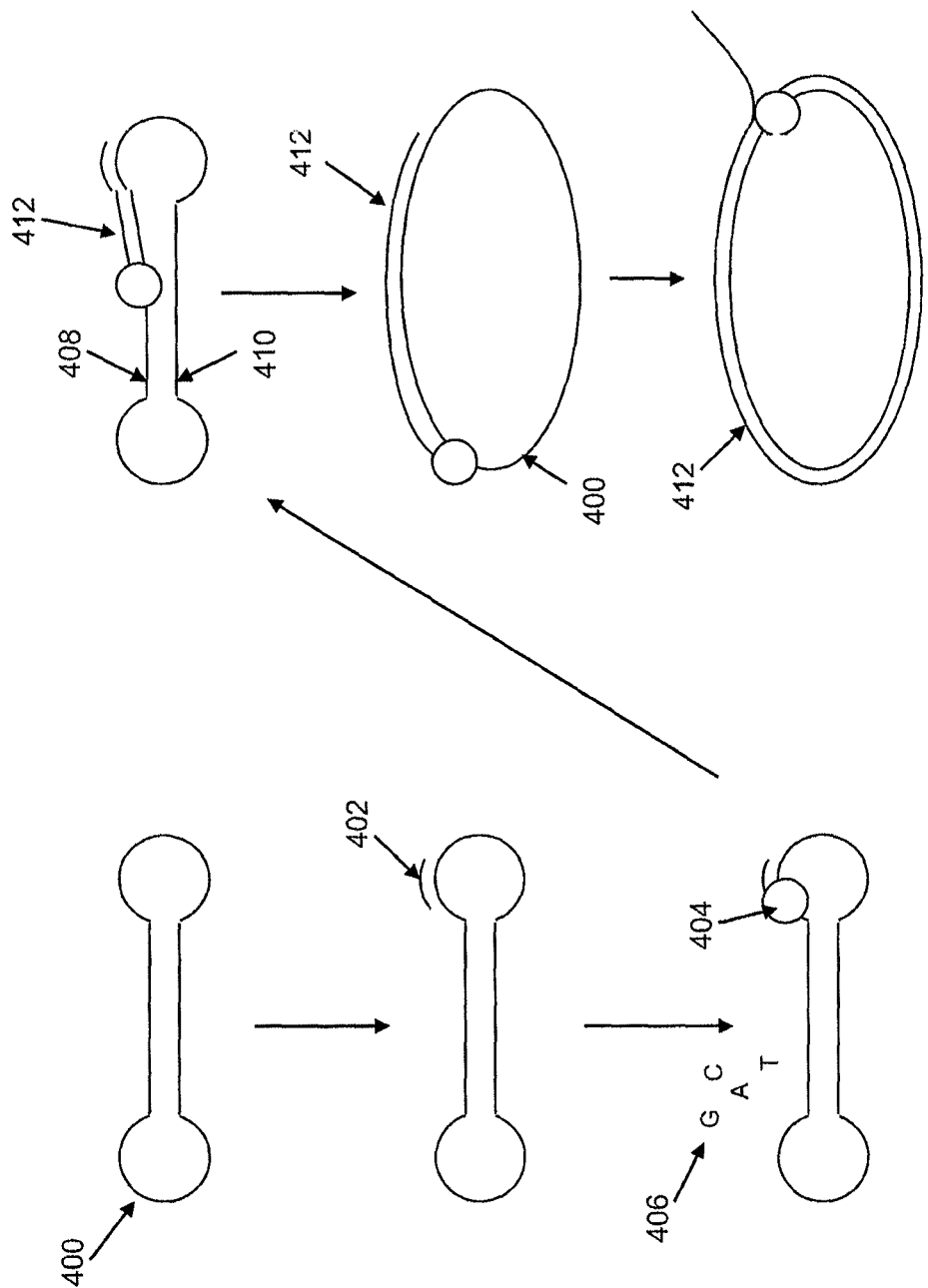
FIG. 4 is a schematic illustration of an amplification method of the invention.

The amplification process for template nucleic acids of the invention and strand displacing enzymes is schematically illustrated in FIG. 4. As shown, a completely contiguous template 400 is complexed with a primer sequence 402 and a strand displacing polymerase 404, and contacted with the four nucleotides 406, or in the case of certain embodiments, nucleotide analogs. As synthesis progresses, the polymerase's own activity displaces one complementary strand 408 from the other 410 and synthesis of the nascent strand 512 continues. Upon complete synthesis, e.g., one full cycle around the template, a double stranded circular sequence results, made up of the original template 400 and the newly synthesized or nascent strand 412. Because the strand displacing enzyme can continue to displace the hybridized strand, e.g., the newly synthesized nascent strand 412, the amplification can continue through the template multiple times to provide multiple copies of the template nucleic acid, typically generating a long, concatamer molecule containing repeated regions complementary to the contiguous template 400.

Alternatively, other mechanisms may be employed to affect strand separation prior to or during synthesis. For example, elevation of the temperature of the reaction mixture may be used to melt the double stranded portion of the template, and permit primer extension through that region. As will be appreciated, for such applications, it may be desirable to employ thermally stable polymerase enzymes that are better suited to the temperatures required for melting, and continued synthesis. A wide variety of thermostable polymerases are known in the art and are applicable to this type of application, including, for example Taq polymerase and its variants.

Figure 5:
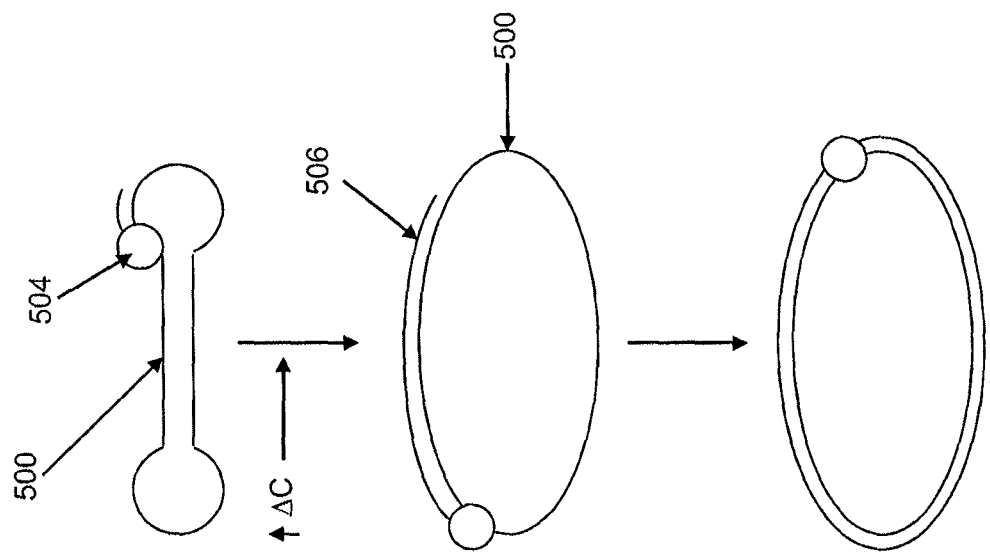
FIG. 5 is a schematic illustration of an amplification method of the invention.

A schematic of synthesis using a thermally regulated amplification process is illustrated in FIG. 5. As shown, a primer 502 is tethered to the template structure 500 and contacted with the non-strand displacing polymerase enzyme 504. Because the template exists in a double stranded configuration and the polymerase is unable to displace the complementary strand, the synthesis does not readily proceed. At a desired point, the double stranded segment is separated to allow synthesis of the nascent strand 506 through the previously double stranded portion of the template 500, e.g., through heating sufficient to melt the double stranded segment without removing the primer (indicated as ΔC). As will be appreciated, primer sequences, as well as additional portions of the linking oligo-nucleotides, may be employed that have relatively higher melting temperatures, e.g., GC rich sequences, that have higher melting temperatures than an average naturally occurring nucleic acid sequence. Once the double stranded segment is duplicated sufficiently to prevent re-hybridization of the original template, by virtue of the presence of the nascent strand, there is no longer a need for denaturation steps or additives.

As will also be appreciated, in the case of the use of non-strand displacing enzymes, additional strand separation steps will typically be needed following one complete cycle around the template, as the nascent strand would then be in position to block continued synthesis. As with initiation of the primer extension, the requirement for another triggering event can provide advantages of synchronizing different template sequence steps. Alternatively, following an initial triggering event, the synthesis reaction may be maintained at elevated temperatures to ensure continuous, uninterrupted amplification of the template nucleic acid.

Application of Affinity Handles

In accordance with any of the embodiments discussed herein, methods of isolating template nucleic acids include in preferred aspects the application of affinity handles to the amplified template nucleic acid.

As discussed above, affinity handles are designed to associate with template nucleic acids. In preferred embodiments, the affinity handles contain capture domains that bind to or hybridize with complement of the target sequence in the template nucleic acid contained in the nascent strand produced by a strand displacing polymerase, thereby "associating with" the template nucleic acids.

In certain embodiments, the affinity handles are applied to the amplified template nucleic acids once the amplification process is complete. In further embodiments, the affinity handles are added to the composition comprising the template nucleic acids prior to or during amplification, such that the affinity handles associate with the complements to the target sequences as those complements generated.

In further embodiments, sets of affinity handles may be applied to a population of template nucleic acids and/or amplified template nucleic acids. Such sets may contain affinity handles which all comprise identical retrieval domains, or the sets may contain mixtures of affinity handles containing different retrieval domains. In further embodiments, different sets of affinity handles are applied to amplified template nucleic acids of the invention, where the affinity handles of one set comprises a different retrieval moiety and/or a different capture domain than the affinity handles of the other sets. As will be appreciated, any number of different sets of affinity handles can be applied to template nucleic acids of the invention, and can be designed to correspond to the number of target sequences of interest or the types of substrates used to capture the affinity handles associated with amplified template nucleic acids.

In further embodiments, a single type of affinity handle comprising a single type of capture region is added to a mixture of polymerase complexes. This is done, for example, where a universal capture region, e.g. on a hairpin adaptor, used for isolating active polymerase-nucleic acid complexes from inactive complexes regardless of sequence. In some cases, a mixture of types of affinity handles is used in which each type of affinity handle has a capture region directed at a different sequence. The mixtures of affinity handles are generally used for isolating nucleic acids having specific sequences from a population of nucleic acids that do not contain such sequences. This method could be directed to pulling down all conserved sequences of genes from a genetic pathway, derived from one organism, but targeted at a second distinct organism. Alternatively, a family of genetic homologs, orthologs and/or paralogs could be targeted for conservation testing. Alternatively, forensic DNA sequencing (e.g., for crime scene investigation) may target a handful of unique identifying sequences in specific loci including, e.g., unique short tandem repeats, which can enable the confident identification of individuals. The number of different affinity handles, each with a different capture sequence, can be from about 2 to about 100,000 or more. In some cases mixtures have from about 5 to about 10,000 or from about 10 to about 1000 different capture regions. The isolation of specific nucleic acid sequences of interest is valuable when greater efficiency of characterization is desired. For example, even with current sequencing technologies, sequencing of whole genomes for many individuals can be impractical. However, by focusing on specific regions of interest, characterization of many genomes can be made more practical. See e.g. Teer J K, Mullikin J C. "Exome sequencing: the sweet spot before whole genomes", Human Molecular Genetics. 2010 Oct. 15; 19(R2):R145-51 and Mamanova L, Coffey A J, Scott C E, Kozarewa I, Turner E H, Kumar A, Howard E, Shendure J, Turner D J. "Target-enrichment strategies for next-generation sequencing" Nature Methods. 2010 February; 7(2):111-8.

In some cases, two or more affinity handles can be employed where the capture region or regions are on one strand of the double-stranded portion. In some cases, two or more affinity handles are employed where the capture region or regions of one or more of the affinity handles is on one strand, and another capture region or region is on the complementary strand.

In some cases in order to capture larger nucleic acid sequences, tiling strategies can be used, whereby sets of shorter oligonucleotides are used with each member of the set targeted to a different portion of the larger nucleic acid sequence. For example, in some cases it could be desired to specifically target a 2 kb sequence of DNA within a library generated by fragmenting genomic DNA. Any given fragment may only have a portion of the 2 kb sequence of interest, so in order to capture such portions, affinity handles are designed to bind to various different portions of the 2 kb sequence can be provided. For example, a tiling strategy could be employed in which a set of capture oligonucleotides was provided for targeting on average, each 50 base region along the 2 kb sequence. This would result in a set of about 40 affinity handles. The nucleic acid portion which is tiled for capture could be from about 100 to greater than 1000 kb long. In some cases it could be between about 1 kb and about 100 kb. The average sequence for each tile can be varied as needed for the application, and could range, for example, from about 20 bases to about 500 bases. The number of capture regions directed at a target sequence can be, for example, from about 10 to about 1000, or from about 20 to about 200. The tiled capture sequences can be used to selectively capture and isolate desired sets of sequences. For example, in some cases, a specific exon, or a specific family of exons could be targeted for isolation. The exons of a specific organism such as human or mouse could be targeted. In some cases, the nucleic acids characteristic of a specific virus, bacterium, or pathogen or a specific strain can be targeted. In other cases nucleic acids representing various functional classes, e.g. those coding for kinases can be targeted for isolation. In some cases, nucleic acids of interest in a particular biological process, such as those implicated in cancer progression or response to drug therapies, can be targeted.

In some cases an iterative capture and retrieval process is employed where a first affinity handle targeting a first target sequence is used to isolate an amplified template nucleic acid having the that sequence, then in a subsequent step, a second affinity handle is used to capture a second target sequence. This results in the isolation of only template nucleic acids having both the first and the second target sequences. In some cases the first and second sequences can be on the same strand of the double stranded portion of the template nucleic acid, and in some cases one sequence is on one strand and the other sequence is on the other strand. In some cases, rather than a single first affinity handle, a set of first affinity handles to capture a set of first target sequences is employed. Analogously, in some cases rather than a second oligonucleotide, a second set of affinity handles is used to capture a set of second target sequences. These iterative isolation and purification methods allow for selecting and isolating only template nucleic acids having a desired set of sequences.

In some embodiments, the affinity handles comprises beads that have two types of capture regions attached to them, a first capture region directed to a first sequence, and a second capture region directed to a second sequence. These beads are added to a solution with a mixture of amplified template nucleic acids, some having only the first or the second target sequence, and some having both the first and the second capture sequence. The stringency of the solution is adjusted such that template nucleic acids only bound through a single interaction will be washed off, but template nucleic acids bound through both the first region and the second region will remain bound to the beads. In preferred embodiments, the template nucleic acids are the amplified template nucleic acids comprising a circular template nucleic acid and a linear nascent strand, as discussed in further detail herein. Applying affinity handles that are beads with two types of capture regions attached to them provides a one-step method for isolating nucleotides from the mixture that have two sequences of interest. In some cases, the two sequences are on the same strand; in some cases, the two sequences are on opposite strands. While this approach is generally used with two types of capture regions on a bead, the same approach can be used employing beads having 3, 4, 5 or more types of capture regions attached to them.

Isolation Steps

In accordance with any of the embodiments discussed herein, methods of the present invention include steps of isolating template nucleic acids containing target sequences of interest from other template nucleic acids in the population.

As discussed above, in preferred aspects, affinity handles of the invention are applied to amplified template nucleic acids and bind or hybridize to complements of the target sequences generated through amplification of the template nucleic acids. The affinity handles comprise retrieval moieties that can be used to isolate the affinity handles and their associated amplified template nucleic acids from the remainder of the template nucleic acids. Since the affinity handles are generally designed to bind to or hybridize with the complements of target sequences of interest, isolating the affinity handles and their associated template nucleic acids serves to isolate template nucleic acids containing target sequences of interest from template nucleic acids that do not contain those target sequences.

As will be appreciated, any coupling groups or binding molecules on a substrate can be used to isolate template nucleic acids through their associated affinity handles. The coupling can be accomplished by forming a covalent bond or through a non-covalent interaction. It is generally desired that the coupling to the substrate result in a strong bond relative to the other linkages, e.g. between the template nucleic acid and the affinity handle. Many types of binding pairs are known in the art. In some cases, an interaction between biotin and a biotin binding protein such as avidin or streptavidin is used. In some cases, an antibody-antigen interaction, for example between digoxigenin and anti-digoxigenin is used. Reactions that form covalent linkages, for example SNAP or Click chemistry can be used to bind the affinity handles to the substrate. Oligonucleotide hybridization can also be used for the attachment. Where such hybridization is used, the linkages are designed such that the oligonucleotide binding to the surface is stronger, e.g. has a higher Tm, than the other linkages between the surface and the remainder of the template nucleic acid to favor binding of affinity handles to the surface over template nucleic acids that are not associated with an affinity handle.

In embodiments in which the retrieval moieties comprise beads or moieties that can attach to beads, methods known in the art to isolate beads from the remaining solution can be used.

The devices, systems, and methods described herein for transferring template nucleic acids onto substrates can also be used to transfer other biomolecules onto substrates and into zero mode waveguides. The methods comprise, for example, attaching a biomolecule or a population of biomolecules to beads, and drawing the beads down to a surface to transfer the biomolecules to the surface. The biomolecules are preferably attached to the beads by association or hybridization such that the attachment can be broken to leave the biomolecule attached to the surface even if the bead is removed from the area. The beads can be magnetic beads that are drawn to the surface and optionally translated with respect to the surface during the loading process as described herein. The surface will generally have reactive components that will react with the biomolecule or with a molecule associated with the biomolecule to attach it to the surface. In some cases, the substrate comprises an array of zero mode waveguides functionalized on the bases of the zero mode waveguides to provide attachment of the biological molecules within the observation region of the zero mode waveguide.

The biological molecules can be any suitable biomolecule including a protein, a nucleic acid, a lipid, a polysaccharide, or a combination of these types of molecules. In some embodiments enzymes are loaded onto the substrate. Many types of enzymes are known in the art that can be used herein. The biological molecules can be constructs made of associated subunits that are bound onto the surface together. For example, the biological molecules can comprise a ribosome. The biological molecules can comprise antibodies or binding proteins. Solid surfaces other than beads can also be used to retrieve the affinity handles having template nucleic acids attached. The solid surfaces can be planar surfaces, such as those used for hybridization microarrays, or the solid surfaces can be the packing of a separation column.

The template nucleic acids bound to the affinity handles can then be further isolated and purified from other components of the reaction once bound to a substrate such as a bead, planar surface, or column. In some embodiments, fluid can be washed over the solid surface, removing components of the original mixture that are not bound to the solid surface, leaving behind on the surface the attached template nucleic acids. This washing can remove, for example, inactive polymerase-nucleic acid complexes, excess enzyme, unbound nucleic acids and other components. The wash fluid will generally contain components that assist in maintaining the stability of the template nucleic acid, e.g. by maintaining levels of specific ions, the required level of ionic strength, and the appropriate pH. The stringency of the medium is also controlled during the wash to ensure that the template nucleic acid remains bound through the associated affinity handle during the wash.

Removal of Linear Strand

In accordance with any of the aspects and embodiments of the invention discussed herein, in certain further aspects the linear nascent strand of the amplified template nucleic acids is removed prior to any subsequent assessment of the template nucleic acid itself.

In preferred embodiments, the amplified template nucleic acid is denatured, for example by heating in formamide, to separate the amplification product (e.g., the nascent strand synthesized using the template nucleic acid as a template) from the original template nucleic acid. In embodiments in which the original template nucleic acid is circular, denaturation will result in a mixture of linear and circular nucleic acids. Treatment with a mixture of single-stranded and double-stranded nucleic acids will remove all amplification products and leave the circular constructs intact, and those circular template nucleic acids can then be utilized in single-molecule sequencing or other types of biochemical analyses.

For example, where the affinity handle comprises an oligonucleotide that is hybridized to the complement of the target sequence of a template nucleic acid, the circular template nucleic acid can be released from the nascent strand (and the associated affinity handle) by raising the stringency of the solution, for example by lowering the ionic strength or raising the temperature. In further embodiments, an exonuclease is applied, which will digest the linear nascent strand but will leave the original circular template nucleic acid intact.

In certain embodiments, both the capture and retrieval regions of affinity handles of the invention bind to their respective targets by nucleic acid hybridization. In such embodiments, one can control which linkage, e.g. the capture linkage or the retrieval linkage is maintained. It is well known that the melting temperature (Tm) of a hybridized portion of oligonucleotides can be adjusted, for example by increasing the number of matched bases, by including unmatched bases, or by including non-natural bases (See, e.g. Sambrook and Russell, Molecular Cloning, a Laboratory Manual, 2001, Cold Spring Harbor Press). Thus the relative strength of linkages can be controlled by controlling the relative Tm. The melting temperature (Tm) is not an absolute value but is dependent on various factors, for example on the ionic strength of the solution. This allows for two linkages to be formed, one having a higher Tm than another, then by controlling the stringency of the solution, one can control whether both of the links, one of the links, or neither of the links are broken.

In a preferred embodiment, the linkage between the capture region of the affinity handle and the complement of the target sequence is designed to have a lower Tm than the linkage between the retrieval region of the affinity handle and the solid substrate. This allows for the stringency of the solution to be lowered in order to release the template nucleic acid from the affinity handle while the linkage between the affinity handle and the solid substrate (e.g. bead) remains intact. The template nucleic acid can then be moved into solution, leaving the affinity handle behind attached to the substrate. In some cases, the Tm of the affinity handle-to-template nucleic acid linkage is between about 2 degrees and about 10 degrees below the Tm of the affinity handle-to-solid substrate (e.g. bead) linkage, in some cases, the Tm of the affinity handle to template nucleic acid linkage is between about 5 degrees and about 50 degrees below the Tm of the affinity handle to solid substrate (e.g. bead) linkage. Since in preferred embodiments the affinity handle is bound through its capture region to a linear strand that is the complement of the template nucleic acid, it will be appreciated that the Tm of the affinity handle to that linear strand can be designed in accordance with the above description.

While in many cases it is desirable to selectively break the linkage between the affinity handle and the template nucleic acid, there may also be cases where it is preferred to selectively break the linkage between the solid substrate and the affinity handle. Such approaches can also be implemented as part of the invention.

VI. Methods of Analyzing Isolated Template Nucleic Acids

The isolated template nucleic acids of the invention can be analyzed using methods known in the art and described herein. In preferred aspects, template nucleic acids isolated in accordance with any of the methods described herein are further analyzed through sequencing methods and/or through identification of one or more modifications of nucleotides in those isolated template nucleic acids. In general, the assessments of the template nucleic acids are focused on the target sequences contained in those template nucleic acids, but the remainder of the template nucleic acids may also be subjected to the assessments in the course of running the reactions.

In preferred embodiments, the template nucleic acids isolated in accordance with the invention as discussed herein contain a targeted population of sequences that are of interest for particular applications. For example, and as is discussed in further detail below, nucleic acids containing specific modification, including methylation, are of particular interest. Other applications include assessing patient samples for the presence of particular viruses or bacteria, assessments for DNA damage, glucosylation, and any other applications for which isolation of a targeted population of nucleic acids is of use.

Another application for template nucleic acids of the invention is to use them to identify genes actively expressed in a sample of interest. In this embodiment, mRNA and genomic DNA are both isolated from a sample. Circular template nucleic acids are prepared from the genomic DNA (in preferred embodiments, the circular template nucleic acids are SMRTbell™ constructs discussed herein). The template nucleic acids are amplified in accordance with the methods described herein. The amplified template nucleic acids are then hybridized to the mRNAs also isolated from the sample. Any number of polyA directed techniques (such as poly dT magnetic beads) can be used to isolate the template nucleic acids that had hybridized to mRNAs—analysis of those isolated template nucleic acids then identifies the genes actively expressed in the sample. Further assessment of those isolated template nucleic acids in accordance with any of the methods discussed herein, particularly the methods for identifying nucleic acid modifications, provides information on the genes actively expressed in the sample.

Further exemplary methods of analyzing isolated template nucleic acids are described below, but as will be appreciated, any assays involving nucleic acids can be used to assess the template nucleic acids isolated in accordance with the methods described herein.

VI.A. Sequence Analysis of Isolated Template Nucleic Acids

In some aspects, the present invention includes methods of analyzing the sequence of template nucleic acids isolated in accordance with the methods described herein. In such aspects, the sequence analysis employs template dependent synthesis in identifying the nucleotide sequence of the template nucleic acid. Nucleic acid sequence analysis that employs template dependent synthesis identifies individual bases, or groups of bases, as they are added during a template mediated synthesis reaction, such as a primer extension reaction, where the identity of the base is required to be complementary to the template sequence to which the primer sequence is hybridized during synthesis. Other such processes include ligation driven processes, where oligo- or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in the ubiquitously practiced four-color Sanger sequencing methods, a population of template molecules is used to create a population of complementary fragment sequences. Primer extension is carried out in the presence of the four naturally occurring nucleotides, and with a sub-population of dye labeled terminator nucleotides, e.g., dideoxyribonucleotides, where each type of terminator (ddATP, ddGTP, ddTTP, ddCTP) includes a different detectable label. As a result, a nested set of fragments is created where the fragments terminate at each nucleotide in the sequence beyond the primer, and are labeled in a manner that permits identification of the terminating nucleotide. The nested fragment population is then subjected to size based separation, e.g., using capillary electrophoresis, and the labels associated with each different sized fragment is identified to identify the terminating nucleotide. As a result, the sequence of labels moving past a detector in the separation system provides a direct readout of the sequence information of the synthesized fragments, and by complementarity, the underlying template (See, e.g., U.S. Pat. No. 5,171,534, incorporated herein by reference in its entirety for all purposes and in particular for all teachings related to nucleic acid sequencing).

Other examples of template dependent sequencing methods include sequence by synthesis processes, where individual nucleotides are identified iteratively, as they are added to the growing primer extension product.

Pyrosequencing is a sequence by synthesis process that identifies the incorporation of a nucleotide by assaying the resulting synthesis mixture for the presence of by-products of the sequencing reaction, namely pyrophosphate. In particular, a primer//template/polymerase complex is contacted with a single type of nucleotide. If that nucleotide is incorporated, the polymerization reaction cleaves the nucleoside triphosphate between the α and β phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. (See, e.g., U.S. Pat. No. 6,210,891, incorporated herein by reference in its entirety for all purposes, and in particular for all teachings related to nucleic acid sequencing).

In related processes, the primer/template/polymerase complex is immobilized upon a substrate and the complex is contacted with labeled nucleotides. The immobilization of the complex may be through the primer sequence, the template sequence and/or the polymerase enzyme, and may be covalent or noncovalent. In general, preferred aspects, particularly in accordance with the invention provide for immobilization of the complex via a linkage between the polymerase or the primer and the substrate surface. A variety of types of linkages are useful for this attachment, including, e.g., provision of biotinylated surface components, using e.g., biotin-PEG-silane linkage chemistries, followed by biotinylation of the molecule to be immobilized, and subsequent linkage through, e.g., a streptavidin bridge. Other synthetic coupling chemistries, as well as non-specific protein adsorption can also be employed for immobilization. In alternate configurations, the nucleotides are provided with and without removable terminator groups. Upon incorporation, the label is coupled with the complex and is thus detectable. In the case of terminator bearing nucleotides, all four different nucleotides, bearing individually identifiable labels, are contacted with the complex. Incorporation of the labeled nucleotide arrests extension, by virtue of the presence of the terminator, and adds the label to the complex. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. (See, e.g., U.S. Pat. No. 6,833,246, incorporated herein by reference in its entirety for all purposes, and in particular for all teachings related to nucleic acid sequencing.)

In yet a further sequence by synthesis process, the incorporation of differently labeled nucleotides is observed in real time as template dependent synthesis is carried out. In particular, an individual immobilized primer/template/polymerase complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a β, γ, or other terminal phosphate group on a nucleoside polyphosphate, the label is not incorporated into the nascent strand, and instead, natural DNA is produced. Observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This results in a characteristic signal associated with the incorporation event, which is also characterized by a signal profile that is characteristic of the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results, that is again, also characteristic of the base being incorporated (See, e.g., U.S. Pat. Nos. 6,917,726, 7,033,764, 7,052,847, 7,056,676, 7,170,050, 7,361,466, 7,416,844, Published U.S. Patent Application No. 2007-0134128, and International Application No. PCT/US2011/060338, filed Mar. 29, 2012, the full disclosures of which are hereby incorporated herein by reference in their entirety for all purposes, and in particular for all teachings related to nucleic acid sequencing).

It will be appreciated that in addition to the sequencing methods described above, the nucleotides or nucleotide analogs may be detectable by any of a variety of different mechanisms including the presence of fluorescent dye labels coupled to the nucleotide through a β, γ or other more distal phosphate group. For example, as alluded to previously, the nucleotides may bear interacting components, such as one or both members of FRET pairs (dyes, semiconductor nanocrystals, or the like) that interact with their complements elsewhere in the system e.g., on the polymerase, primer, the nucleotide itself, or the substrate. Similarly, these nucleotide analogs may bear other interactive components, such as energy donors or quenchers that alter signal capability of other proximal components. Likewise, non-optical labels may be employed, such as highly charged moieties, magnetic particles or the like, that may be detected by electrochemical systems, e.g., ChemFET sensors, nanopore sensors (see, e.g., Clarke et al., Nature Nanotechnology, Published online: 22 Feb. 2009|doi:10.1038/nnano.2009.12), and the like. In addition, the nucleoside polyphosphates described herein may generally include tri, tetra, penta, hexa or other phosphate chain lengths incorporatable by the polymerases used. Such compounds, including those bearing detectable labeling groups are described in, e.g., U.S. Pat. No. 7,041,812, the full disclosure of which is incorporated herein by reference in its entirety for all purposes and in particular for all teachings related to detectable labeling groups.

For a number of approaches, e.g., single molecule methods as described above, it may be desirable to provide the nucleic acid synthesis complexes in individually optically resolvable configurations, such that the synthesis reactions of a single complex can be monitored. Providing such complexes in individually resolvable configuration can be accomplished through a number of mechanisms. For example, by providing a dilute solution of complexes on a substrate surface suited for immobilization, one will be able to provide individually optically resolvable complexes (See, e.g., European Patent No. 1105529 to Balasubramanian, et al., which is incorporated herein by reference in its entirety for all purposes, and in particular for all teachings related to single molecule sequencing methods.) Alternatively, one may provide a low density activated surface to which complexes are coupled (See, e.g., Published International Patent Application No. WO 2007/041394, the full disclosure of which is incorporated herein by reference in its entirety for all purposes). Such individual complexes may be provided on planar substrates or otherwise incorporated into other structures, e.g., zero mode waveguides or waveguide arrays, to facilitate their observation.

Pooled sample methods are also envisioned by the present invention. For example, in some aspects, the methods of the invention comprise preparing template nucleic acids from each of a plurality of discrete nucleic acid samples, wherein the template nucleic acids comprise double stranded segments of the nucleic acid samples, a first strand of the double stranded segment being linked to a second strand of the double stranded segment by a linking oligonucleotide, wherein the linking oligonucleotide in each discrete nucleic acid sample comprises a unique, identifiable sequence characteristic. The template nucleic acids from the plurality of discrete nucleic acid samples are then pooled, and the pooled template nucleic acids comprising target sequences of interest are isolated in accordance with the description herein and are then sequenced to identify the identifiable sequence characteristic, and the nucleic acid sequences deriving from the discrete nucleic acid samples are identified based at least in part on the unique identifiable sequence characteristic identified in the sequencing step.

Figure 3A:
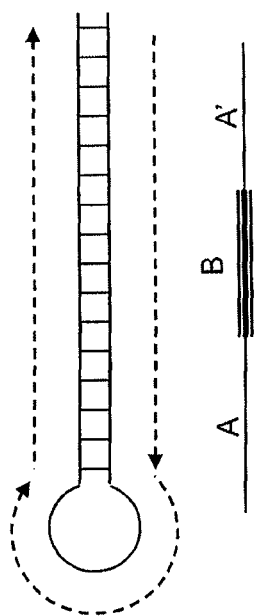
FIG. 3A-B are schematic illustrations of sequencing methods of the invention.

The progress of sequencing processes is schematically illustrated in FIG. 3A. In particular, as shown, a sequencing process that begins, e.g., is primed, at the open end of the partially contiguous template, proceeds along the first or sense strand, providing the nucleotide sequence (A) of that strand, as represented in the schematic sequence readout provided. The process then proceeds around the linking oligonucleotide of the template, providing the nucleotide sequence (B) of that segment. The process then continues along the antisense strand to the A sequence, and provides the nucleotide sequence (A'), which sequence can be used to derive or determine a consensus sequence for the sense strand, as its antisense counterpart. As noted, because the B sequence may be exogenously provided, and thus known, it may also provide a registration sequence indicating a point in the sequence determination at which the sequencing reaction, and thus, the sequence data being obtained from the overall template construct, transitions from the sense to the antisense strands.

Figure 3B:
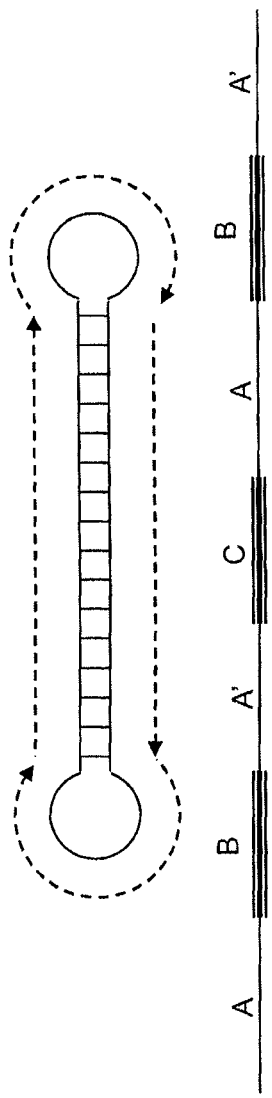

With respect to completely contiguous or circular template sequences configured in accordance with the invention, the potential for obtaining replicate sequence read data from which one may assemble consensus sequence information, is further increased. In particular, as with the partially contiguous sequences shown in FIG. 2A, the completely contiguous sequences also provide sense and antisense sequence data. In addition, such templates provide for the potential for iterative sequencing of the same molecule multiple times, by virtue of the circular configuration of the template. Restated, a sequence process may progress around the completely contiguous sequence repeatedly obtaining sequence data for each segment from the complementary sequences, as well as sequence data within each segment, by repeatedly sequencing that segment. All or portions of such sequence data are then useful in deriving a consensus sequence for the template and its various segments. This is schematically illustrated in FIG. 3B, again with a representative illustration of a sequence readout provided. As shown, a sequencing process that is primed at one end, e.g., primed within one linking oligonucleotide sequence, e.g., linking oligonucleotide 218 of FIG. 2, proceeds along the first or sense strand 214, again providing the nucleotide sequence A of that strand. The sequence process then proceeds around the first linking oligonucleotide, e.g., linking oligonucleotide 216 from FIG. 2, to provide the nucleotide sequence B of that segment of the template. Proceeding along the antisense strand, e.g., segment 212 of FIG. 2B, provides the nucleotide sequence A', which is again, complementary to sequence A. The sequencing process then continues around the template providing the nucleotide sequence for the other linking oligonucleotide, e.g., linking oligonucleotide 218 of FIG. 2B, where the illustrated sequencing process began, providing nucleotide sequence C. Because the template is circular, this process can continue to provided multiple repeated sequence reads from the one template, e.g., shown as providing a second round of the sequence data (A-B-A'-C-A-B-A'). Thus, sequence redundancy comes from both the determination of complementary sequences A and A', and the repeated sequencing of each segment.

As will be appreciated, in iteratively sequencing circular templates, strand displacing polymerases, as discussed elsewhere herein, are particularly preferred, as they will displace the nascent strand with each cycle around the template, allowing continuous sequencing. Other approaches will similarly allow such iterative sequencing including, e.g., use of an enzyme having 5'-3' exonuclease activity in the reaction mixture to digest the nascent strand post synthesis.

Methods for sequencing template nucleic acid sequences, particularly circular template nucleic acids, are known in the art and described for example in US 20110281768, filed on Feb. 1, 2011, which is hereby incorporated by reference in its entirety for all purposes and in particular for all teachings related to sequencing of circular template nucleic acids.

VI.B. Detection of Modified Nucleic Acid Sequences

In certain aspects, the present invention is directed to the detection of modified nucleic acid sequences, and particularly the detection of methylated bases within nucleic acid sequences using a real time direct detection of such methylated sites.

In certain aspects of the invention, methods are provided for identification of a modification in a template nucleic acid isolated in accordance with the methods described herein. In general, the template nucleic acid comprising the modification and an enzyme capable of processing the template are provided. The template nucleic acid is contacted with the enzyme, and the subsequent processing of the template by the enzyme is monitored. A change in the processing is detected, and this change is indicative of the presence of the modification in the template. Examples of changes in the processing of the template by the enzyme that are monitored in various embodiments of the invention include, but are not limited to, kinetics, processivity, affinity, rate, strand-displacement activity, signal characteristics, error metrics, signal context, and the like. In some embodiments, a change occurs only at the modification, and in other embodiments the change occurs at one or more positions proximal to the modification, which may also include the modification position.

Exemplary modifications that can be detected by the methods of the invention include, but are not limited to methylated bases (e.g., 5-methylcytosine, $N^6$-methyladenosine, etc.), pseudouridine bases, 7,8-dihydro-8-oxoguanine bases, 2'-O-methyl derivative bases, base J, s4U, s6G, nicks, apurinic sites, apyrimidic sites, pyrimidine dimers, a cis-platen crosslinking products, oxidation damage, hydrolysis damage, bulky base adducts, thymine dimers, photochemistry reaction products, interstrand crosslinking products, mismatched bases, secondary structures, and bound agents. In preferred embodiments, nucleotides or analogs thereof that are incorporated into a nascent strand synthesized by the enzyme are distinctly labeled to allow identification of a sequence of specific nucleotides or nucleotide analogs so incorporated. In certain preferred embodiments, labels are linked to nucleotides or nucleotide analogs through a phosphate group, e.g., a phosphate group other than the alpha phosphate group. As such, the labels are removed from the nucleotide or nucleotide analog upon incorporation into the nascent strand.

In some embodiments, the template nucleic acid is treated prior to processing by the enzyme, e.g., to alter the modification. The treatment may be chemical or enzymatic, and includes, e.g., glycosylase modification, bisulfite modification, DMS modification, cytosine methyltransferase modification, hydroxylation, TET1 modification, and cytidine deaminase modification. In some embodiments, non-natural nucleotide analogs (e.g., pyrene analogs) are incorporated into a nascent strand synthesized by the enzyme. In some embodiments, the methods comprise both treatment of the template and incorporation of non-natural nucleotide analogs into the nascent strand. In some embodiments, non-natural nucleotides are incorporated into a nascent strand in a position to pair with a modification in the template. For example, a methylated cytosine in the template can be paired with a modified guanine nucleotide analog; a template modification can pair with a non-natural nucleotide analog to form a non-natural base pair, e.g., isocytosine and isoguanine; 5-methyl-isocytosine and isoguanine; Im-$N^O$ and Im-$O^N$; A* and T*; and 8-oxoG and adenine. In some embodiments, non-incorporatable nucleotide analogs bind the template/enzyme complex, but are not incorporated into the nascent strand, and detection of this "nonproductive" binding serves as an indication of the modification in the template. Such non-incorporatable nucleotide analogs are preferably distinctly labeled to facilitate monitoring, and optionally to distinguish such binding from incorporation of incorporatable nucleotide analogs that comprise labels.

As discussed in further detail herein, in certain embodiments, the template nucleic acid comprises regions of internal complementarity (e.g., a double-stranded portion) and at least one single-stranded portion, and preferably the modification is located within at least one of the regions of internal complementarity. In certain embodiments, the template is a circular template. In certain embodiments, the template is a circular template comprising at least two regions of internal complementarity. In certain embodiments, the enzyme is a polymerase, such as a DNA polymerase, and RNA polymerase, a reverse transcriptase, or a derivative or variant thereof. In preferred embodiments, the enzyme is a polymerase enzyme capable of strand displacement. In specific embodiments, the enzyme is a Φ29 polymerase, optionally comprising at least one mutation at a position selected from the group consisting of K392, K422, I93, M188, K392, V399, T421, K422; S95, Y101, M102; Q99, L123, K124, T189, A190; G191, S388; P127, L384, N387, S388; and L389, Y390, and G391.

In certain aspects, the methods further comprise mapping the modification. In certain preferred embodiments, mapping the modification comprises analyzing a portion of the sequence read that was generated immediately prior to, during, and/or immediately after detecting the change in processing to determine a sequence complementary to the template nucleic acid; determining the complement of the sequence complementary to the template nucleic acid; and mapping the modification at a position in the template nucleic acid that is proximal to the complement of the sequence complementary to the template nucleic acid.

In certain embodiments, a change in the processing that is indicative of the modification is a kinetic difference in the processing (e.g., detected as an alteration in one or more of interpulse duration, interpulse width, processivity, cessation of processing, etc.) and/or a change in an error metric (e.g., accuracy, an increase in binding events that do not result in incorporation, etc.) The change in processing can be indicative of the type of modification is present in the template nucleic acid, since different types of modifications have different effects on the activity and/or fidelity of the enzyme.

In preferred embodiments, the monitoring occurs in real time during the processing of the template by the enzyme. In preferred embodiments, the template nucleic acid and the enzyme form a complex that is immobilized at a reaction site on a substrate, and in more preferred embodiments a plurality of complexes are immobilized at optically resolvable reaction sites on the substrate, wherein a single complex immobilized at one of the reaction sites is optically resolvable from any other of the complexes immobilized at any other of the reaction sites. In certain embodiments, the optically resolvable reaction sites are nanometer-scale apertures in the substrate, and can be optical confinements, such as zero-mode waveguides. In preferred embodiments, the template nucleic acid is plurality of template nucleic acids that are optically resolvable from one another during the monitoring. Preferably, the template nucleic acid is not amplified prior to contacting it with the enzyme.

In some embodiments, the modification is secondary structure in the template nucleic acid, e.g., a hairpin loop, supercoiling, internal hybridization, etc., and the change in the modification is a kinetic change, e.g., an increased interpulse duration or increased pulse width. Certain methods for identifying such a secondary structure generally comprise generating a sequence read for the template nucleic acid before, during, and after the kinetic change; identifying a first portion of the sequence read generated before and/or during the kinetic change that is complementary to a second portion of the sequence read generated during and/or after the kinetic change; and determining a likelihood that the first and second portions may have been annealed in the template nucleic acid during the processing, e.g. to form a hairpin loop, based at least upon the nucleotide composition of the first portion and the second portions.

In another aspect of the invention, methods for detecting binding of an agent to a single template nucleic acid are provided. In certain embodiments, such methods generally comprise providing the single template nucleic acid in complex with a polymerase; introducing a reaction mixture to the complex, wherein the reaction mixture comprises the agent; and monitoring synthesis of a polynucleotide by the polymerase, wherein the polynucleotide is complementary to the single template nucleic acid, and wherein a change in the synthesis is indicative of binding of the agent to the single template nucleic acid. Examples of agents appropriate for use in such methods include, but are not limited to, transcription factors, polymerases, reverse transcriptases, histones, restriction enzymes, antibodies, nucleic acid binding proteins, and nucleic acid binding agents. Examples of single template nucleic acids appropriate for use in such methods include, but are not limited to, double-stranded DNA, double-stranded RNA, single-stranded DNA, single-stranded RNA, DNA/RNA hybrids, and templates comprising both double-stranded and single-stranded regions.

In certain aspects of the invention, a consensus binding site of the agent is determined. This determination can comprise, e.g., performing a plurality of sequencing-by-synthesis reactions on a set of single template nucleic acids in the presence of the agent to generate a set of binding-affected nascent polynucleotide sequences; performing a plurality of sequencing-by-synthesis reactions on the set of single template nucleic acids in the absence of the agent to generate a set of full-length nascent polynucleotide sequences; analyzing the binding-affected nascent polynucleotide sequences to determine a location at which the agent bound the single template nucleic acid during the sequencing-by-synthesis reactions in the presence of the agent; and identifying a sequence common to the full-length nascent polynucleotide sequences at the location, thereby identifying the consensus binding site of the agent. In certain embodiments, the binding-affected nascent polynucleotide sequences are truncated nascent polynucleotide sequences; and in other embodiments, the binding-affected nascent polynucleotide sequences are nascent polynucleotide sequences whose synthesis was paused at the location at which the agent bound.

In yet further aspects of the invention, methods for detecting modifications in a single template nucleic acid during a sequencing-by-synthesis reaction are provided. For example, such a method can comprise providing the single template nucleic acid in complex with a polymerase; introducing a reaction mixture to the complex, wherein the reaction mixture comprises an agent that specifically binds to the modification; and monitoring synthesis of a polynucleotide by the polymerase, wherein the polynucleotide is complementary to the single template nucleic acid, and wherein a pause or cessation of the synthesis of the polynucleotide is indicative of binding of the agent to the single template nucleic acid, thereby detecting the modification in the single template nucleic acid. In certain embodiments, the modification is an 8-oxoG lesion and/or the agent is a protein selected from the group consisting of hOGG1, FPG, yOGG1, AlkA, Nth, Nei, MutY, UDG, SMUG, TDG, NEIL, an antibody against 8-oxoG, or a binding domain thereof. In other embodiments, the modification is a methylated base and/or the agent is a protein selected from the group consisting of MECP2, MBD1, MBD2, MBD4, UHRF1, an antibody against the methylated base, or a binding domain thereof. In further embodiments, the modification is a secondary structure formation in the template nucleic acid. Preferably, the complex is immobilized in an optical confinement. The template can comprise, e.g., single-stranded linear nucleic acid, single-stranded circular nucleic acid, double-stranded linear nucleic acid, double-stranded circular nucleic acid, or a combination thereof.

In certain embodiments, a modification in a template nucleic acid can be repaired by including components of damage repair machinery in the reaction mixture, e.g., during a sequencing-by-synthesis reaction. In certain embodiments, the readlength of the sequencing-by-synthesis reaction is longer than that for a further sequencing-by-synthesis reaction performed with the single template nucleic acid in complex with the polymerase, but absent the agent and the damage repair machinery.

In other aspects of the invention, methods for bypassing one or more modifications in a single template nucleic acid during a sequencing-by-synthesis reaction are provided. Certain exemplary methods include providing the template nucleic acid in complex with a sequencing engine; introducing a reaction mixture to the complex, wherein the reaction mixture comprises a bypass polymerase; initiating the sequencing-by-synthesis reaction; monitoring synthesis of a polynucleotide by the sequencing engine, wherein the polynucleotide is complementary to the template nucleic acid, and wherein a pause or cessation of the synthesis of the polynucleotide is indicative that the sequencing engine has encountered a modification in the template; subsequently monitoring synthesis of the polynucleotide by the bypass polymerase, which is indicative that the modification is being bypassed; and repeating the monitoring steps each time a further modification is encountered in the single template nucleic acid, thereby bypassing one or more modifications in a single template nucleic acid during a sequencing-by-synthesis reaction. In certain embodiments, the bypass polymerase comprises a detectable label and detection of a signal from the detectable label during the sequencing-by-synthesis reaction is indicative that the bypass polymerase is actively synthesizing the polynucleotide. In preferred embodiments, the readlength of the sequencing-by-synthesis reaction is longer than that for a further sequencing-by-synthesis reaction performed with the single template nucleic acid in complex with the sequencing engine, but absent the bypass polymerase. In specific embodiments, the reaction mixture comprises multiple different bypass polymerases and a processivity factor. Preferably, at least one of the template nucleic acid, the sequencing engine, and the bypass polymerase is immobilized, directly or indirectly, in an optical confinement. For example, the template can be immobilized by hybridization to an oligonucleotide primer immobilized in the optical confinement. In certain preferred embodiments, the template nucleic acid is processed by the sequencing engine multiple times at a single reaction site, and further wherein redundant sequence data is generated.

In further aspects of the invention, systems for identification of modifications within a template nucleic acid are provided. In certain preferred embodiments, a system of the invention comprises a solid support having a polymerase complex disposed thereon (e.g., at a reaction site, e.g., in a nanoscale aperture, e.g., in a zero-mode waveguide), the polymerase complex comprising an isolated template nucleic acid of the invention comprising a modification; a mounting stage configured to receive the solid support; an optical train positioned to be in optical communication with at least a portion of the solid support to detect signals emanating therefrom; a translation system operably coupled to the mounting stage or the optical train for moving one of the optical train and the solid support relative to the other; and a data processing system operably coupled to the optical train. Preferably, the polymerase complex comprises a polymerase enzyme that is actively processing the template nucleic acid. More preferably, the polymerase complex comprises a polymerase enzyme that is processively synthesizing a nascent strand by template-directed synthesis. In preferred embodiments, the optical train detects signals emanating from the solid support during the processing of the template nucleic acid.

In certain aspects, the invention provides method for identifying modifications within template nucleic acids isolated in accordance with the descriptions provided herein, the method for identifying modifications comprising introducing a further modification into a template nucleic acid already comprising a modification of interest. An enzyme processes the template nucleic acid, and the processing of the template by the enzyme is monitored. Changes in the processing are indicative of the further modification, and therefore, indirectly, the modification of interest is identified. The modification of interest can be any modification useful for directing or marking the template to facilitate introduction of the further modification. For example, the modification of interest can be chosen from the following: a methylated base, a hydroxymethylated base, HOMedU, β-D-glucosyl-HOMedU, cytosine-5-methylenesulfonate, a pseudouridine base, an 7,8-dihydro-8-oxoguanine base, a 2'-O-methyl derivative base, a nick, an apurinic site, an apyrimidic site, a pyrimidine dimer, a cis-platen crosslinking, oxidation damage, hydrolysis damage, a bulky base adduct, a thymine dimer, a photochemistry reaction product, an interstrand crosslinking product, a mismatched base, a secondary structure, and a bound agent. In some preferred embodiments, the template nucleic acid comprises a single-stranded portion and a double-stranded portion, and in some cases the double-stranded portion is a result of complementarity between two separate portions of the template nucleic acid. In some embodiments, the template nucleic acid comprises a first polynucleotide region comprising the modification and a second polynucleotide region complementary to the first polynucleotide region, where the first polynucleotide region and the second polynucleotide region are on a single strand of the template nucleic acid, e.g., in different regions of a single-stranded circular template nucleic acid. Typically, the template nucleic acid is subjected to a treatment to introduce the further modification, and such a treatment can comprise exposure to a modifying agent, e.g., a glycosylase, bisulfite, DMS, a cytosine methyltransferase, a hydroxylase (e.g., TET1 protein), a restriction enzyme, a glucosyltransferase, NMIA, CDI, and a cytidine deaminase. For example, the treatment can comprise exposure to bisulfite that converts 5-hmC to CMS in the template. The treatment can also comprise addition of a sugar moiety (e.g., sucrose, glucose, maltose, galactose, dextrose, lactose, etc.) or group to a nucleobase comprising the modification. The addition of the sugar moiety serves to increase the response of the enzyme, e.g., polymerase, resulting in a greater change is processing that would occur in the absence of the sugar moiety. For example, the nucleobase can be a hydroxymethylcytosine nucleobase, which is converted to β-glucosyl-5-hydroxymethylcytosine by the addition of the sugar moiety. Addition of the sugar moiety can occur via an alpha or beta linkage. Further, a plurality of sugar moieties can be added. In further embodiments, the treatment comprises replacement of the modification with the further modification, e.g., when the modification is a methylated base and the further modification is an abasic site or a pyrene analog. In certain preferred embodiments, the processing of the template is monitored for kinetic changes, which can be indicative of a modification or a further modification. The template nucleic acid can be RNA or DNA, or can comprise both ribo- and deoxyribonucleotides, is preferably not amplified. The enzyme is preferably a polymerase enzyme, e.g., a DNA polymerase, and RNA polymerase, a reverse transcriptase, or a derivative thereof. Preferably, the processing is a sequencing reaction (e.g., a single-molecule sequencing reaction), and where the template is a closed circular template and the polymerase is capable of strand displacement, the processing can comprise rolling-circle replication of the template, which can generate redundant sequence data for the template. The change in processing can occur at the modification or further modification, or can occur at one or more positions upstream or downstream of the modification (also referred to herein as a "primary" modification to identify a modification originally present in the nucleic acid as opposed to an "introduced" or "further" modification) or further modification, and can be a kinetic change such as an alteration in interpulse duration or pulse width. The change in processing is preferably indicative of the type of modification and/or further modification present in the template. In certain embodiments, mapping the modification further comprises analyzing a portion of the sequence read that was generated immediately prior to, during, or immediately after the detecting the change in processing to determine a sequence complementary to the template nucleic acid; determining the complement of the sequence complementary to the template nucleic acid in f; and mapping the modification at a position in the template nucleic acid that is proximal to the complement of the sequence complementary to the template nucleic acid in f. In preferred embodiments, the monitoring occurs in real time during the processing. In further aspects, the template nucleic acid and enzyme form a complex that is immobilized at a reaction site on a substrate, and a plurality of such complexes can be immobilized at optically resolvable reaction sites on the substrate. Optionally, these optically resolvable reaction sites are nanometer-scale apertures in the substrate, preferably with optical confinement properties, e.g., such as zero-mode waveguides.

Methods are also provided for mapping binding sites of binding agents bound to or previously bound to a template nucleic acid. In certain embodiments, a method of mapping a binding site comprises exposing a single template nucleic acid to a binding agent, subjecting the template to a template-directed synthesis reaction, and monitoring the reaction for a change indicative of the binding site. The binding agent can be any agent that binds to the template, including transcription factors, polymerases, reverse transcriptases, histones, restriction enzymes, antibodies, nucleic acid binding proteins, nucleic acid binding agents, and nucleic acid damage binding agents. The single template nucleic acid is typically one of a double-stranded DNA, a double-stranded RNA, a single-stranded DNA, a single-stranded RNA, a DNA/RNA hybrid, and a combination thereof. In certain embodiments, the methods further comprise crosslinking the binding agent to the single template nucleic acid prior to the template-directed synthesis, and in some cases the crosslinking is photoactivatable crosslinking Optionally, prior to the template-directed synthesis the crosslinked binding agent can be removed from the single template nucleic acid, e.g., by protease or other degradative treatment. In certain embodiments, the change in the synthesis reaction is detected at or proximal to a remnant of the crosslinking that remains on the template nucleic acid after removal of the binding agent. In some embodiments, an affinity purification is performed to isolate portions of the template nucleic acid to which the binding agent is associated, e.g., after crosslinking Optionally, the single template nucleic acid can comprise thiol-modified nucleosides, e.g., 4-thiouridine, 6-thioguanosine, 2-thiocytosine, or 4-thiothymidine. In certain embodiments, the binding agent is linked to a modifying agent that introduces a modification into the single template nucleic acid proximal to the binding site, and further wherein the modification causes the change in the synthesis. A modifying agent linked to a binding agent can be one or more reactants that introduce modifications into a nucleic acid, e.g., methyltransferases, glycosylases, glucosytransferases, hydroxylases (e.g., TET1), and nucleic acid damaging agents. For example, a Dam adenine methyltransferase linked to a transcription factor will convert adenosine to N6-methyladenosine at loci proximal to the binding site of the transcription factor. In certain embodiments, a plurality of different binding agents can be assayed simultaneously, e.g., with each linked to a different modifying agent such that the detection of a particular modification in the template is indicative of the binding of a particular one of the binding agents proximal to that modification. Optionally, where the nucleotide sequences of binding sites for multiple different binding agents are distinct from one another, the same modifying agent can be linked to the different binding agents. In such an embodiment, the presence of a modification indicates there was a binding event, and nucleotide sequence information from that region coupled with prior knowledge of the consensus binding sites for the binding agents informs as to which binding agent was bound. The sequence data is preferably generated during the monitoring of the template-directed synthesis reaction, e.g., in real time. In further embodiments, both sequence data and modification detection and identification are used in combination to determine a binding site of a binding agent linked to a modifying agent. Preferably, the single template nucleic acid is in an optical confinement, e.g., a zero mode waveguide.

In yet further aspects, the invention provides methods for mapping a modification in an isolated template nucleic acid that comprise splitting the population of isolated template nucleic acids and subjecting different portions of the population to different treatments and/or manipulations. For example, a single population comprising multiple template nucleic acid molecules having a modification at a particular locus can be divided into two aliquots. A first aliquot is subjected to an amplification reaction that does not maintain the modification in the amplicons, and the second aliquot is not amplified. Both aliquots are subjected to a sequencing reaction, together or separately, and the nucleotide sequence reads generated are analyzed to determine the locus at which the modification occurred, that is, to "map" the modification. A optional procedure can be employed to enrich the nucleic acids comprising the modification in the single nucleic acid sample. For example, a binding agent that specifically binds the modification can be used to select the molecules having the modification by forming a binding agent/modification complex that is retained, e.g., by immobilization, while the nucleic acids not bound to the binding agent (e.g., those not comprising the modification) are removed. The selected template nucleic acids are subsequently subjected to sequencing, e.g., after being released from the binding agents, or optionally, with the binding agents still bound to enhance the response of the polymerase to the modification site. The enrichment procedure can occur before or after the amplification of the first aliquot. In yet further embodiments, barcode sequences are added to nucleic acids in one or both aliquots. These barcodes are sequenced along with the template, and they serve to identify the source of a particular template, e.g., whether it came from the first or second aliquot. For example, a first barcode can be included in the template nucleic acids in the first aliquot (e.g., before or after amplifications), and a second barcode can be included in the template nucleic acids in the second aliquot. The two aliquots are combined and sequenced in a single sequencing reaction mixture and the sequence data generated not only provides information about the location of any modifications, but also provides the barcode sequence data to identify the source of the template. Preferably, the sequencing reactions are performed on single, optically resolvable templates to produce a separate individual sequence read for each template molecule.

In yet further aspects, the invention provides machine-implemented methods for transforming reaction data into modification detection data, wherein the reaction data is representative of a series of events during a sequencing-by-synthesis reaction wherein a nascent strand is synthesized based upon a nucleotide sequence of a template nucleic acid, and the modification detection data is representative of a presence of one or more modifications within a template nucleic acid. Preferably, one or more steps of the machine-implemented method are performed via a user interface implemented in a machine that comprises instructions stored in machine-readable medium and a processor that executes the instructions. In a final aspect of the invention, a computer program products are provided. In certain embodiments, machine-implemented methods for transforming reaction data comprise a classifier to distinguish between true incorporations and stochastic pulses, a segmenting algorithm based on a hidden Markov model architecture, and/or a segmenting algorithm based on a conditional random field framework. In certain specific embodiments, the methods identify regions in the template having a higher density of stochastic pulses than true incorporations. In certain specific embodiments, the methods identify regions in the template having higher IPD. Exemplary computer program products of the invention typically comprise a computer usable medium having a computer readable program code embodied therein, said computer readable program code adapted to be executed to implement the machine-implemented methods of the invention; and the machine-readable medium on which the results of one or more steps of the machine-implemented method are stored.

EXAMPLES

Example 1

The genomic DNA of interest is first converted to SMRTbell format as illustrated in FIG. 4, item 400. Primers complimentary to the single stranded region (FIG. 4, item 402) are added to the sample SMRTbells in a 2:1 molar ratio and annealed by heating the sample to 80° C. and cooled to room temperature at 0.1° C. per second. Annealed sample, typically at a concentration near 10 nM, is bound to a 3-fold molar excess of Phi29 polymerase in a buffer containing 50 mM TrisCl, 100 mM KCl, 0.2 mM $CaCl_2$, 10 mM DTT, 0.05% (w/v) Tween-20, and 1 uM dNTPs at pH 7.5. After 30 min of binding at room temperature, primers are extended for 5 min by the addition of $MgCl_2$ to 10 mM, dNTPs to 10 uM and a 5-fold molar excess of the biotinylated capture oligonucleotide. Magnetic streptavidin beads with at least two-fold excess binding capacity over the quantity of primer are used to capture the biotinylated oligonucleotide and washed extensively with 50 mM TrisCl, 100 mM KCl, and 0.05% (w/v) Tween-20. SMRTbell samples are eluted from the beads by heating the sample to 90° C. and cooling the sample to room temperature at 2° per minute, releasing the nascent strands and associated capture oligonucleotides. The supernatant is treated extensively with exonuclease to digest residual oligonucleotides and nascent products, leaving the unmodified target samples in the solution.

While the foregoing invention has been described in some detail for purposes of clarity and understanding, it will be clear to one skilled in the art from a reading of this disclosure that various changes in form and detail can be made without departing from the true scope of the invention. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method for isolating circular template nucleic acids containing one or more target sequences from a mixture of nucleic acids, said method comprising:
   (a) providing a population of nucleic acid constructs, said constructs comprising circular template nucleic acids, wherein a plurality of said circular template nucleic acids comprises said one or more target sequences;
   (b) amplifying said population of nucleic acid constructs with a strand displacing polymerase to produce amplified template nucleic acids, wherein said amplified template nucleic acids each comprise one of said circular template nucleic acids hybridized to a linear nascent strand comprising at least one copy of a sequence complementary to said one or more target sequences;
   (c) associating one or more affinity handles with said amplified template nucleic acids, wherein said one or more affinity handles comprises an affinity oligonucleotide moiety and a retrieval moiety, wherein said affinity oligonucleotide moiety hybridizes to said at least one copy of a sequence complementary to said one or more target sequences;
(d) separating amplified template nucleic acids associated with said affinity handles from amplified template nucleic acids not associated with said affinity handles using said retrieval moieties;
(e) after said separating, treating said amplified template nucleic acids such that said circular template nucleic acids are separated from said linear nascent strands; and
(f) isolating said circular template nucleic acids containing one or more target sequences from the mixture of nucleic acids.

2. The method of claim 1, wherein said population of nucleic acid constructs comprises genomic DNA.

3. The method of claim 1, wherein said circular template nucleic acids comprise a single-stranded portion and a double-stranded portion.

4. The method of claim 1, wherein said nucleic acid constructs are single stranded or double stranded.

5. The method of claim 1, wherein said nucleic acid constructs comprise:
(a) a first strand segment,
(b) a second strand segment substantially complementary to said first strand segment;
(c) a first linking oligonucleotide segment joining the 3' end of said first strand segment to the 5' end of said second strand segment;
(d) a second linking oligonucleotide segment joining the 5' end of said first strand segment to the 3' end of said second strand segment.

6. The method of claim 1, wherein said affinity handles comprises an oligonucleotide or a protein capable of binding to a nucleic acid.

7. The method of claim 1, wherein said affinity handles comprise an oligonucleotide.

8. The method of claim 7, wherein said oligonucleotide comprises deoxynucleotide bases, ribonucleotide bases, or a combination of both deoxynucleotide and ribonucleotide bases.

9. The method of claim 7, wherein said oligonucleotide comprises modified nucleotide bases.

10. The method of claim 7, wherein said oligonucleotide further comprises a moiety that is a member selected from: biotin, a magnetic bead, a second oligonucleotide, an organic molecule, a polypeptide, a nucleic acid binding dye, a particle, an antibody.

11. The method of claim 1, wherein said treating step (e) comprises heating said amplified template nucleic acids to separate said circular template nucleic acids from said linear amplification products.

12. The method of claim 1, wherein said treating step (e) comprises applying an exonuclease such that said linear nascent strands are digested, leaving only said circular template nucleic acids.

13. The method of claim 1, wherein said amplifying step (b) is allowed to proceed for a sufficient amount of time such that said linear nascent strand comprises multiple copies of said sequences complementary to said one or more target sequences.

* * * * *